(12) United States Patent
Hatanaka et al.

(10) Patent No.: US 7,858,112 B2
(45) Date of Patent: Dec. 28, 2010

(54) PERCUTANEOUS ABSORPTION SYSTEM AND PERCUTANEOUS ABSORPTION METHOD

(75) Inventors: Tomio Hatanaka, Gunma (JP); Rui Saito, Saitama (JP); Kenji Sugibayashi, Saitama (JP); Kiyose Nakagawa, Saitama (JP)

(73) Assignees: Lintec Corporation, Tokyo (JP); Kenji Sugibiayashi, Saitama (JP)

( * ) Notice: Subject to any disclaimer, the term of this patent is extended or adjusted under 35 U.S.C. 154(b) by 833 days.

(21) Appl. No.: 10/372,957

(22) Filed: Feb. 26, 2003

(65) Prior Publication Data
US 2003/0161869 A1 Aug. 28, 2003

(30) Foreign Application Priority Data
Feb. 28, 2002 (JP) .............................. 2002-052925
Feb. 28, 2002 (JP) .............................. 2002-052933

(51) Int. Cl.
*A61K 9/70* (2006.01)
(52) U.S. Cl. .................... 424/449; 600/577; 604/185; 604/290; 604/156; 604/306; 604/304
(58) Field of Classification Search .................. None
See application file for complete search history.

(56) References Cited

U.S. PATENT DOCUMENTS

| | | | | |
|---|---|---|---|---|
| 3,367,332 A | * | 2/1968 | Groves | 604/290 |
| 4,117,841 A | * | 10/1978 | Perrotta et al. | 604/304 |
| 4,808,172 A | * | 2/1989 | Murata | 604/306 |
| 4,880,416 A | * | 11/1989 | Horiuchi et al. | 424/448 |
| 4,988,341 A | * | 1/1991 | Columbus et al. | 604/306 |
| 5,147,337 A | * | 9/1992 | Plone | 604/306 |
| 5,201,324 A | * | 4/1993 | Swierczek | 600/583 |
| 5,616,132 A | * | 4/1997 | Newman | 604/185 |
| 5,636,640 A | * | 6/1997 | Staehlin | 600/577 |
| 6,165,155 A | * | 12/2000 | Jacobsen et al. | 604/156 |
| 6,190,367 B1 | * | 2/2001 | Hall | 604/290 |
| 6,562,014 B2 | * | 5/2003 | Lin et al. | 604/317 |
| 6,719,734 B1 | * | 4/2004 | Harkless | 604/201 |
| 2003/0083619 A1 | * | 5/2003 | Angel et al. | 604/141 |

FOREIGN PATENT DOCUMENTS

| | | |
|---|---|---|
| JP | 57-55157 | 1/1982 |
| JP | 57175114 | 10/1982 |
| JP | 62-112557 A | 5/1987 |
| JP | 62-298375 A | 12/1987 |
| JP | 06-79002 A | 3/1994 |
| JP | 7-255845 | 10/1995 |
| JP | 07-255845 | * 10/1995 |
| JP | 08-509200 A | 10/1996 |
| JP | 09-124468 | 5/1997 |
| JP | 11509123 | 8/1999 |
| JP | 2002 060349 | 2/2002 |
| WO | 90/07328 | 7/1990 |
| WO | 97/03718 | 2/1997 |
| WO | 98/16208 | 4/1998 |

OTHER PUBLICATIONS

Merriam-Webster Online Dictionary, posted on Feb. 3, 2007.*
Human translation of JP 09-124468, The McElroy Translation Company, Sep. 2009.*
Human translation of JP 2002-060349, Schreiber Translations, Inc., Sep. 2009.*
English abstract of JPH09-124468 A, published May 13, 1997.
English abstract of JPS57-55157 A, published Jan. 4, 1982.
English abstract of JPS57-175114 A, published Oct. 28, 1982.
English abstract of JP2002-060349 A, published Feb. 26, 2002.
English Language Abstract of JP 6-79002, Mar. 22, 1994.
English Language Abstract of JP 7-255845, Oct. 9, 1995.

* cited by examiner

*Primary Examiner*—Robert A Wax
*Assistant Examiner*—Hasan S Ahmed
(74) *Attorney, Agent, or Firm*—Greenblum & Bernstein, P.L.C.

(57) ABSTRACT

The present invention provides a percutaneous absorption system and a percutaneous absorption method, which have a simple constitution and can realize the easy and continuous percutaneous absorption of medicine even when the medicine is formed of a water-soluble oligomer solution or a high-molecular solution. In the percutaneous absorption system comprising a medicine reservoir portion having a medicine holding portion which holds medicine therein and a support portion for supporting the medicine reservoir portion, the support portion including an adhesive layer and a substrate having medicine non-permeating property, the system is provided with an elastic member for applying pressure to the medicine held in the inside of the medicine reservoir portion, and by breaking the substrate having medicine non-permeating property in the support portion using a mechanical stimulus such as an injection needle or the like, the medicine is released (delivered) at a fixed rate.

18 Claims, 20 Drawing Sheets

PRIOR ART

PRIOR ART

PERCUTANEOUS ABSORPTION SYSTEM AND PERCUTANEOUS ABSORPTION METHOD

BACKGROUND OF THE INVENTION

1. Field of the Invention

The present invention relates to a percutaneous absorption system and a percutaneous absorption method, and more particularly to a percutaneous absorption system and a percutaneous absorption method which enable an easy and continuous percutaneous absorption of medicine even when the medicine is formed of an oligomer or a high-molecular compound which are not generally suitable for percutaneous absorption.

2. Description of the Related Art

As an administration method of medicine in a situation where an immediate effectivity is desired, an injection is a typical example. Further, recently, a non-needle injection method adopting a jet injector which feeds medicine (medicine in a liquid form) in a human or animal body by making use of water pressure has been developed and has been served for clinical applications such as a subcutaneous injection of insulin.

However, when the injection or the jet injector is used, the medicine is temporarily injected into the body and hence, to sustain the medicine efficacy continuously, there has been a drawback that the administration must be performed frequently.

Further, as a sustainable or continuous medicine administration method, there have been proposed various types of percutaneous absorption systems including a percutaneous absorption system which is comprised of a reservoir for medicine (medicine in a liquid form) and an adhesive layer and a percutaneous absorption system which is comprised of a reservoir for medicine, a delivery control film which controls a delivery quantity of medicine and an adhesive layer.

For example, in JP7-255845A, there is disclosed a medicine administration method which uses a jet injector. To explain the method more specifically, as shown in FIG. 19, this publication discloses a percutaneous absorption system 100 which includes a jet injector 102 for forming a hole in a stratum corneum of skin by making use of water pressure, a reservoir 112 for storing medicine 106, a medicine-permeable adhesive layer 110 for closing an opening portion formed by the jet injector 102, wherein a rubber member 104 for closing an opening portion formed by the jet injector 102 is provided to a ceiling portion of the reservoir 112. The publication also discloses a method for promoting the percutaneous absorption of medicine using the percutaneous absorption system 100.

In such a percutaneous absorption system 100, the opening is formed in a surface of skin (not shown in the drawing) by way of the reservoir 112 and the adhesive layer 110 using the jet injector 102 and the medicine is percutaneously absorbed in the body through the opening portion by making use of the difference in concentration between the medicine in the reservoir 112 and the medicine in a blood vessel.

Further, in the JP11-509123A, as shown in FIG. 20, there is disclosed a percutaneous absorption system for delivering medicine. The percutaneous absorption system includes a reservoir 210 for storing active substance 208, which constitutes the medicine and a large number of micro-pins 206 or micro-blades for administrating the active substance, wherein openings 204 are formed in distal end portions of the micro-pins 206 or the micro-blades.

In such a percutaneous absorption system, a large number of micro-pins 206 or micro-blades formed on a bottom face of the reservoir 210 are pushed into a stratum corneum of a skin and, basically by making use of the diffusion of medicine attributed to the difference in concentration between the medicine in the reservoir 210 and the medicine in the blood vessel, the active substance 208 which constitutes the medicine is percutaneously absorbed in a human body or an animal body by way of openings 204 formed in the distal end portions of a large number of micro-pins or the like.

However, according to the percutaneous absorption system 100 and the percutaneous absorption promoting method of medicine using the percutaneous absorption system 100 disclosed in JP7-255845A, although the hole is formed in the stratum corneum of the skin surface, since the diffusion of medicine is performed basically by making use of the difference in concentration of medicine, there is a case that a penetration quantity of medicine is in short or insufficient. Particularly, when the medicine is formed of an oligomer or a high-molecular compound, it may be difficult to achieve the rapid penetration of medicine.

Further, according to the percutaneous absorption system 200 disclosed in JP11-509123A, the movement of the medicine 208 is performed only by the difference in concentration. Accordingly, although there may arise no serious problem in the movement of the medicine when the medicine is a low-molecular compound having a polarity, when the medicine is formed of an oligomer or the high molecular compound, it has been difficult to achieve the percutaneous absorption of the medicine.

Further, when a large number of micro-pins 206 or the micro-blades are pushed into a skin, the opening portions 204 formed in the distal end portions thereof are clogged and hence, it has been difficult to deliver the medicine 208 at a fixed rate.

Still further, since it is necessary to provide a large number of micro-pins 206 or micro-blades, it may be difficult to manufacture the percutaneous absorption system 200 and a length of the micro-pins 206 or the like is restricted so that the medicine cannot be delivered to the inside of the stratum corneum.

Additionally, according to a preferred embodiment of the percutaneous absorption system 200 disclosed in JP11-509123A, the introduction of a pump or a piezoelectric film into the system of the percutaneous absorption system 200 is proposed. In this case, however, there arises a new problem that the percutaneous absorption system becomes large-sized and hence, the portability and the economical aspect are deteriorated.

In view of the above circumstances, to solve the above-mentioned drawbacks, the inventors of the present invention have extensively studied the problems and have made a following finding as a result of the study. That is, by applying pressure to medicine by way of a medicine holding portion and by breaking a substrate using a mechanical stimulus such as an injection needle or the like, it is possible to provide a percutaneous absorption system which exhibits the excellent portability and the excellent adhesiveness while enabling the continuous and rapid percutaneous absorption of medicine with respect to a largely different types of medicines. The present invention is completed based on such a finding.

That is, it is an object of the present invention to provide a percutaneous absorption system, which has a simple structure and enables an easy and continuous percutaneous absorption of medicine even when the medicine is formed of an oligomer or a high-molecular compound and a percutaneous absorption method, which uses such a percutaneous absorption system.

SUMMARY OF THE INVENTION

According to the first aspect of the present invention, there is provided a percutaneous absorption system comprising a medicine reservoir portion having a medicine holding portion which holds medicine therein and a support portion for supporting the medicine reservoir portion, the support portion including an adhesive layer and a substrate having medicine non-permeating property, wherein a portion or the whole of the medicine reservoir portion is constituted of an elastic member (resilient member) for applying pressure to the medicine held in the medicine holding portion, and the substrate having medicine non-permeating property in the support portion is breakable upon receiving a mechanical stimulus.

Further, in constituting the percutaneous absorption system according to the present invention, it is preferable that the mechanical stimulus is a mechanical stimulus given from the outside of the percutaneous absorption system.

Further, in constituting the percutaneous absorption system according to the present invention, it is preferable that the mechanical stimulus is a mechanical stimulus given by a projection provided in the inside of the medicine reservoir portion.

Further, in constituting the percutaneous absorption system according to the present invention, it is preferable that the elastic member is a foamed body.

Further, in constituting the percutaneous absorption system according to the present invention, it is preferable that the medicine reservoir portion has a substantially cylindrical shape and defines the medicine holding portion in the inside thereof.

Further, in constituting the percutaneous absorption system according to the present invention, it is preferable that the projection has a distal end portion thereof extended downwardly and arranged substantially in the direction perpendicular to the substrate having medicine non-permeating property.

Further, in constituting the percutaneous absorption system according to the present invention, it is preferable that the projection is mounted on an upper surface of the medicine reservoir portion and the upper surface of the medicine reservoir portion is formed of an elastic member.

Further, in constituting the percutaneous absorption system according to the present invention, it is preferable that a pushing portion, which is served for pushing down the projection, is formed on an end portion of the projection.

Further, according to another aspect of the present invention, there is provided a percutaneous absorption system comprising a medicine reservoir portion having a medicine holding portion which holds medicine therein and a support portion for supporting the medicine reservoir portion, the support portion including an adhesive layer and a substrate having medicine non-permeating property, wherein bubbles which apply pressure to the medicine held in the medicine holding portion are introduced in the inside of the medicine holding portion and the substrate having medicine non-permeating property in the support portion is breakable upon receiving a mechanical stimulus.

Further, in constituting the percutaneous absorption system according to the present invention, a portion or the whole of the medicine reservoir portion is constituted of an elastic member for applying pressure to the medicine held in the medicine holding portion.

According to still another aspect of the present invention, there is provided a percutaneous absorption method which uses a percutaneous absorption system comprising a medicine reservoir portion having a medicine holding portion which holds medicine therein and a support portion for supporting the medicine reservoir portion, the support portion including an adhesive layer and a substrate having medicine non-permeating property, wherein the method comprises a step for mounting the percutaneous absorption system, a step for breaking at least the substrate having medicine non-permeating property in the support portion using a mechanical stimulus, and a step for delivering the medicine by applying pressure to the medicine using an elastic member provided to the medicine reservoir portion.

According to a further aspect of the present invention, there is provided a percutaneous absorption method which uses a percutaneous absorption system comprising a medicine reservoir portion having a medicine holding portion which holds medicine therein and a support portion for supporting the medicine reservoir portion, the support portion including an adhesive layer and a substrate having medicine non-permeating property, wherein the method comprises a step for mounting the percutaneous absorption system, a step for breaking at least the substrate having medicine non-permeating property in the support portion using a mechanical stimulus, and a step for delivering the medicine by applying pressure to the medicine using bubbles introduced into the medicine reservoir portion.

BRIEF DESCRIPTION OF THE DRAWINGS

FIGS. 7(a) and 7(b) are views for explaining the structure of a percutaneous absorption system adopting a plurality of medicine reservoir portions.

DESCRIPTION OF THE PREFERRED EMBODIMENTS

Preferred embodiments related to a percutaneous absorption system and a percutaneous absorption method according to the present invention are specifically explained hereinafter in conjunction with drawings suitably.

First Embodiment

Figure 1:
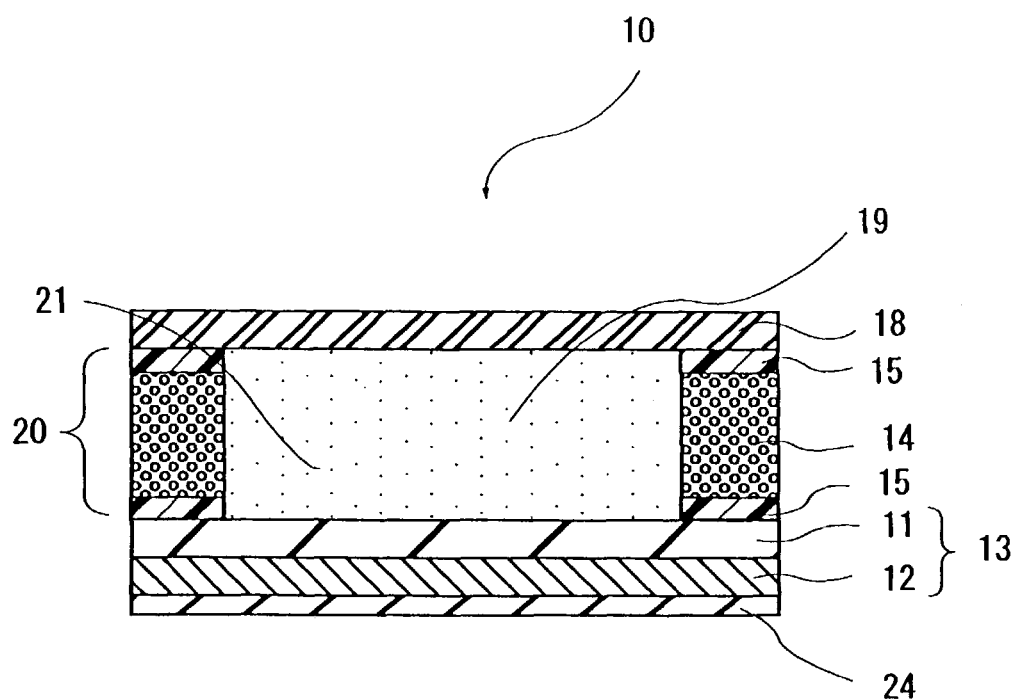
FIG. 1(a) is a view for explaining the structure of a percutaneous absorption system adopting an elastic member and FIG. 1(b) is a view for explaining a manner of using the percutaneous absorption system adopting an elastic member.
Figure 1:
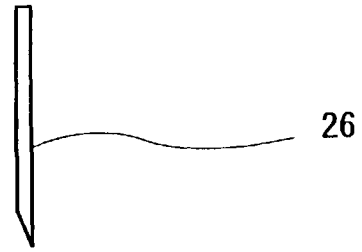
Figure 1:
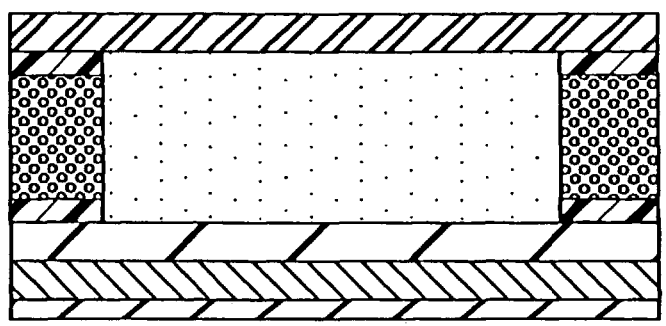

The first embodiment is directed, as illustrated in FIG. 1, to a percutaneous absorption system 10 which includes a medicine reservoir portion 20 having a medicine holding portion 21 which holds medicine 19 therein, a support portion 13 for supporting the medicine reservoir portion 20 which is comprised of an adhesive layer (first adhesive layer) 12 and a substrate 11 having medicine non-permeating property (first substrate having medicine non-permeating property), wherein a portion or the whole of the medicine reservoir portion 20 is constituted of an elastic member for applying pressure to the medicine 19 held in the medicine holding portion 21 by way of the medicine holding portion 21 and the substrate 11 having medicine non-permeating property in the support portion 13 is breakable upon receiving a mechanical stimulus.

Hereinafter, respective constitutional features of the percutaneous absorption system are specifically explained.

1. Medicine Reservoir Portion (1) Configuration

It is preferable that the medicine reservoir portion 20 is configured such that, in a state that the pressure is applied to the medicine, the medicine 19 can be held in the medicine holding portion for a fixed time and, when at least the substrate having medicine non-permeating property is broken, the medicine 19 can be delivered. Further, it is preferable that the medicine reservoir portion 20 is configured such that the configuration facilitates the manufacturing of the medicine reservoir portion 20. Accordingly, it is preferable that a contour of the medicine reservoir portion 20 adopts a substantially rectangular shape shown in FIG. 1 to FIG. 3 or a substantially cylindrical shape shown in FIG. 4 to FIG. 6. In FIG. 4 to FIG. 6, to facilitate the understanding of the inner state of the cylindrical medicine reservoir portion 20, a perspective cross-section in a two-split state is shown.

Further, as shown in FIG. 1, a sidewall of the medicine reservoir portion 20 is formed of an elastic member (resilient member) 14. Here, assuming that the contour of the medicine reservoir portion 20 has substantially the cylindrical shape or the rectangular shape, it is usually preferable to set a thickness of the sidewall to a value which falls within a range of about 1 to 10 mm and to set a height of the sidewall to a value which falls within a range of about 1 to 50 mm.

Here, the medicine is usually used as medicine in a liquid form by mixing or dispersing the medicine in a solvent such as water, ethanol or the like. In this case, although the concentration of the medicine can be suitably selected, it is usually preferable to set the concentration of the medicine to a value which falls within a range of about 0.01 to 90 weight % with respect to a total quantity and it is more preferable to set the concentration of the medicine to a value which falls within a range of about 0.1 to 50 weight % with respect to a total quantity.

(2) Medicine

Although the type of the medicine held in the medicine holding portion 21 is not particularly restricted, for example, nitroglycerine (angina pectoris medicine), nitric acid iso sorbitol (angina pectoris medicine), clonidine (hyper tension medicine), tulobutenol (bronchial asthma medicine), eperisone (muscular pain medicine), salicyclic acid (muscular pain medicine), estradiol (hormone), fentanyl (cancer pain relaxation reagent) scopolamine (motion sickness stop medicine), lidocaine (anesthetic), nicotine (smoking cessation adjuvant) and the like may be used in a single form or in combination of two or more types.

Further, with respect to the type of medicine, the medicine made of an oligomer or a high-molecular compound, which is generally not suitable for percutaneous absorption, may be also used. That is, even when the medicine is formed of an oligomer or a high-molecular compound having a number-average molecular weight of about 500 to 100,000, particularly even when the medicine is formed of a water-soluble oligomer or a high-molecular compound, it is possible to make such medicine penetrate a skin. As examples of such medicine, insulin (antidiabetic), calcitonin (osteoporosis treatment medicine), vasopressin (diuretic) and the like are named.

Further, in the medicine stored in the medicine holding portion, a given quantity of an absorption promoter such as alcohols, glycols, vegetable oil or the like may be added.

(3) Pressure Applying Conditions

Although it is preferable to determine the pressure applying condition of the medicine by taking types, viscosity, concentration and the like of the medicine into account, for example, it is preferable to set an initial pressure of the medicine to a value which falls within a range of about $1.05 \times 10^5$ to $2 \times 10^5$ Pa.

The reason is that when the initial pressure of the medicine assumes a value below $1.05 \times 10^5$ Pa, there may be a case that the permeating speed of the medicine is remarkably lowered in case the medicine is formed of an oligomer or a high-molecular compound, while when the initial pressure of the medicine exceeds $2 \times 10^5$ Pa, there may be a case that the permeating speed of the medicine is remarkably increased or the medicine holding portion breaks.

Accordingly, it is more preferable to set the initial pressure of the medicine to a value which falls within a range of about $1.1×10^5$ to $1.8×10^5$ Pa. It is further more preferable to set the initial pressure of the medicine to a value which falls within a range of about $1.2×10^5$ to $1.7×10^5$ Pa.

(4) Osmotic Pressure

Further, it is preferable to set an osmotic pressure of the medicine in the medicine holding portion to a value higher than an osmotic pressure of a body fluid. The reason is that by making use of not only the delivery of the medicine 19 due to the application of pressure but also the osmotic pressure of the medicine 19, it is possible to easily obtain the continuous percutaneous absorption of the medicine even when the medicine is formed of an oligomer or a high-molecular compound which is not generally suitable for the percutaneous absorption.

Here, to be more specific, it is preferable to set the osmotic pressure of the medicine 19 to a value, which falls within a range of about 300 to 500 mOsm.

(5) Division Type

Figure 7:
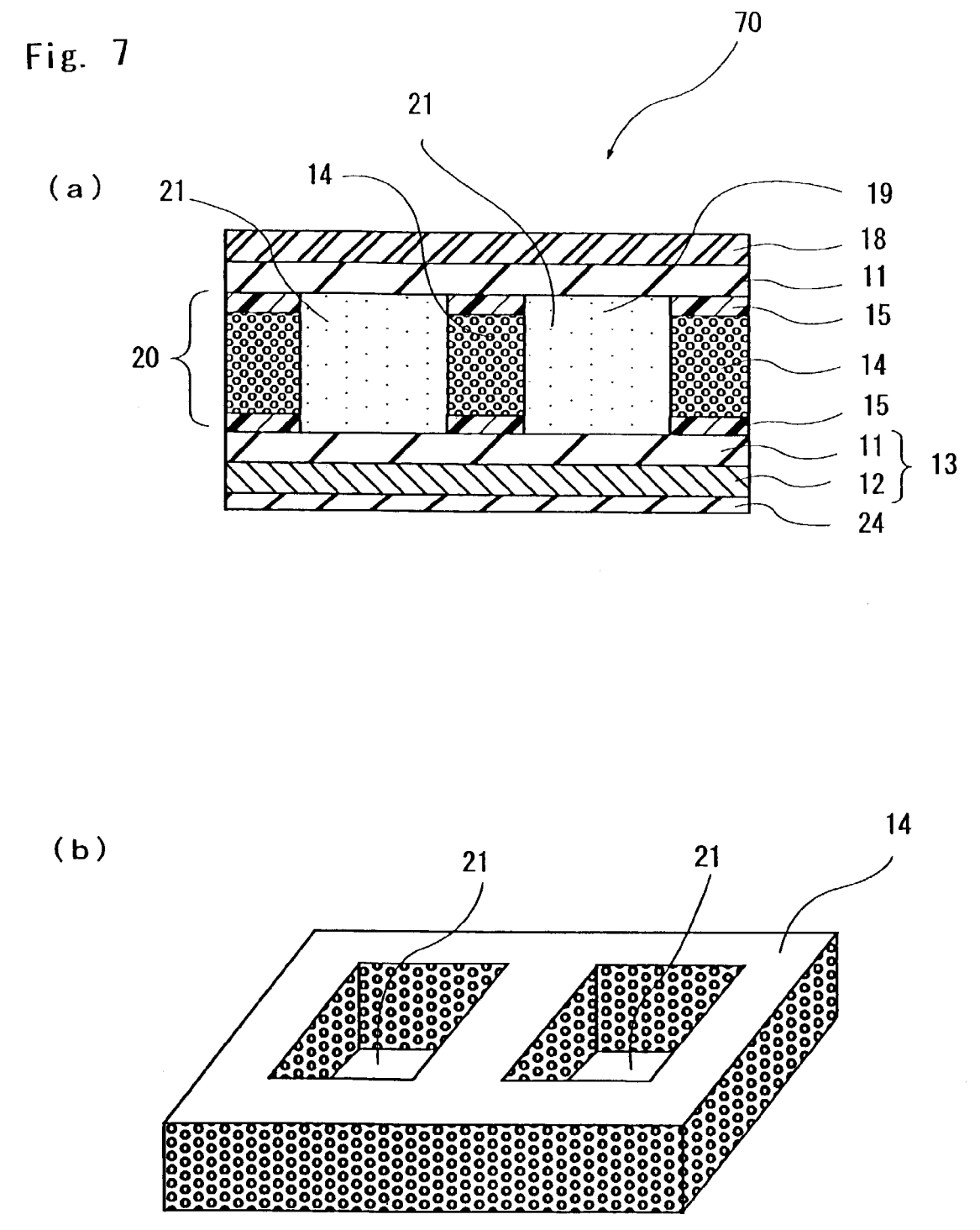

Further, as shown in FIG. 7 (a), it is possible to provide a percutaneous absorption system 70, which is provided with a medicine holding portion 21 consisting of a plurality of, for example, 2 to 10 cells by dividing the medicine reservoir portion 20.

As shown in FIG. 7 (b), a perspective view of a sidewall formed of an elastic member 14 having two space portions is shown to facilitate the understanding of the constitution of the medicine reservoir portion 20 and the medicine holding portion 21.

2. Support Portion (1) Constitution

The support portion is, as shown in FIG. 1, provided for supporting the medicine reservoir portion 20 provided with the medicine holding portion 21 in which the medicine 19 is held and is constituted of an adhesive layer 12 and the substrate 11 having medicine non-permeating property. Although the structure of the support portion is not restricted provided that at least the substrate 11 having medicine non-permeating property can be broken by the mechanical stimulus such as an injection needle or the like, the support portion can be adhered to the medicine reservoir portion 20 by means of the adhesive layer 12. Furthermore, it is preferable to constitute the support portion such that the leaking of the medicine in a liquid form can be prevented even when the medicine 19 is under a pressurized state and the medicine reservoir portion 20 can maintain a given shape.

Figure 2:
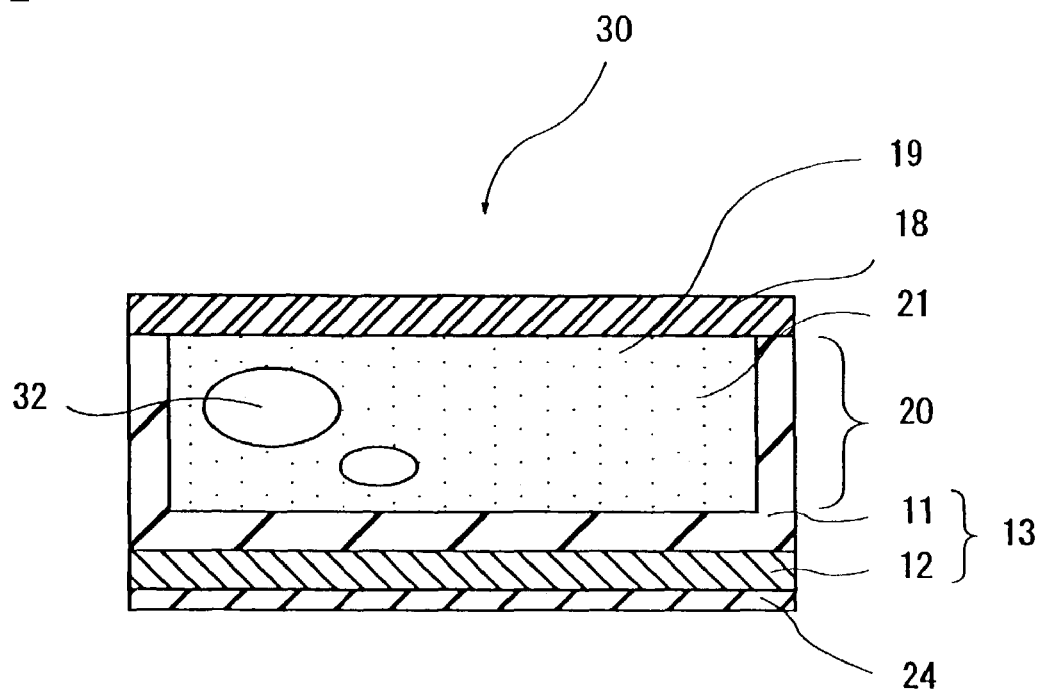
FIG. 2(a) is a view for explaining the structure of a percutaneous absorption system adopting bubbles and FIG. 2(b) is a view for explaining a manner of filling bubbles into the inside of the percutaneous absorption system.
Figure 2:
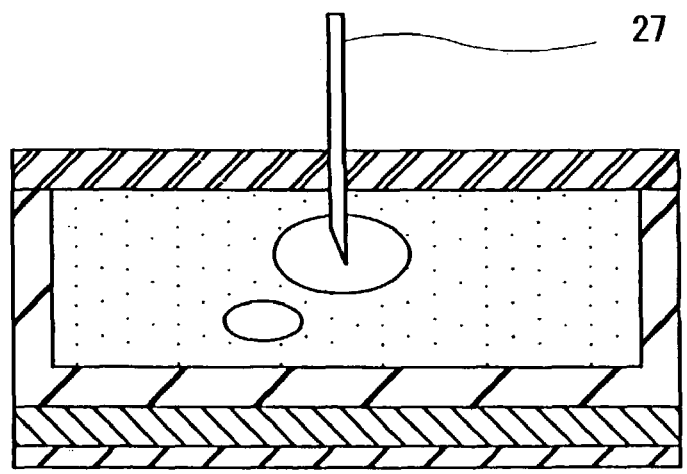
Figure 3:
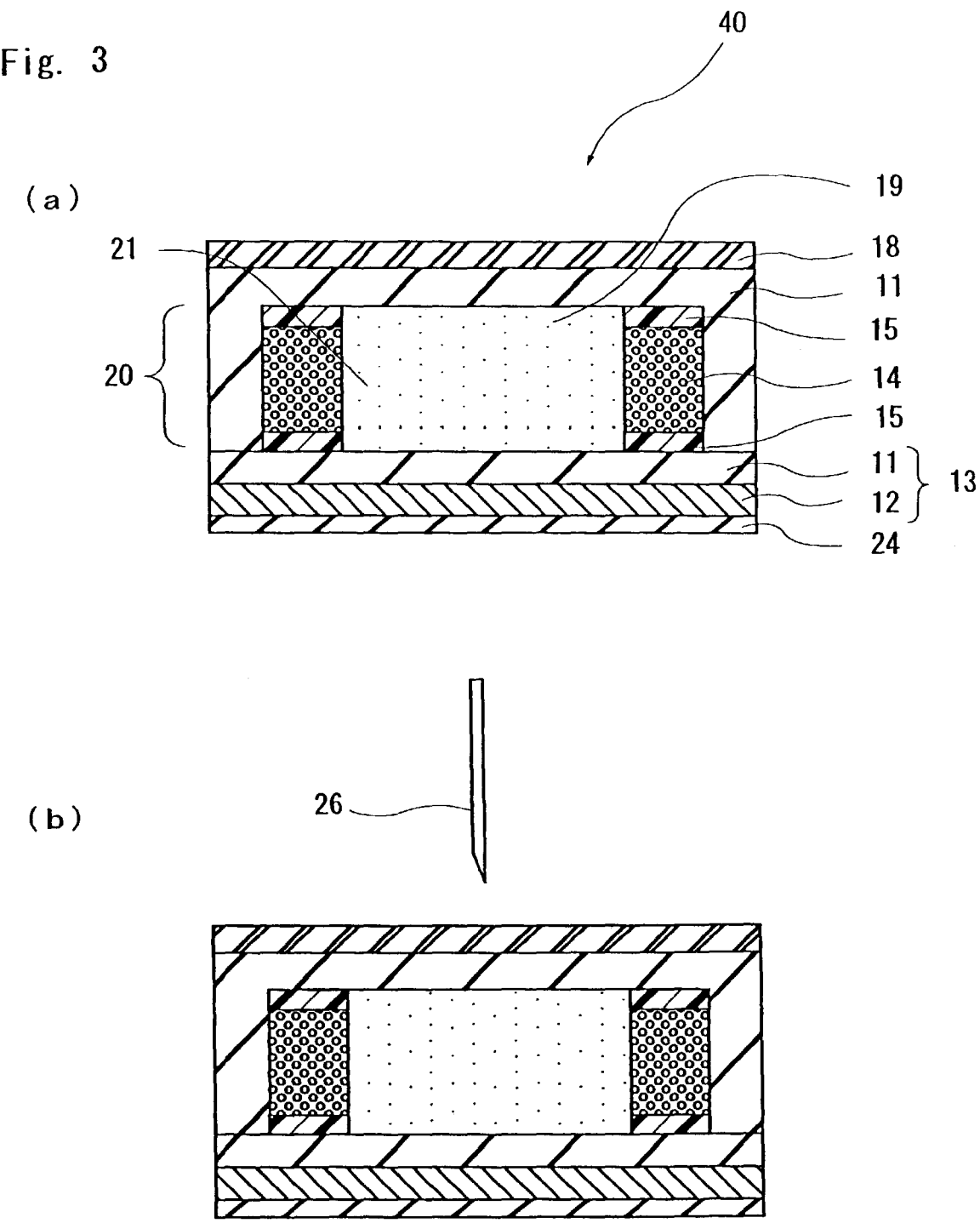
FIG. 3(a) is a view for explaining the structure of a percutaneous absorption system, which differs from previous embodiments with respect to the arrangement of a substrate
FIG. 3(b) is a view for explaining a manner of using the percutaneous absorption system, which differs from previous embodiments with respect to the arrangement of a substrate.
Figure 4:
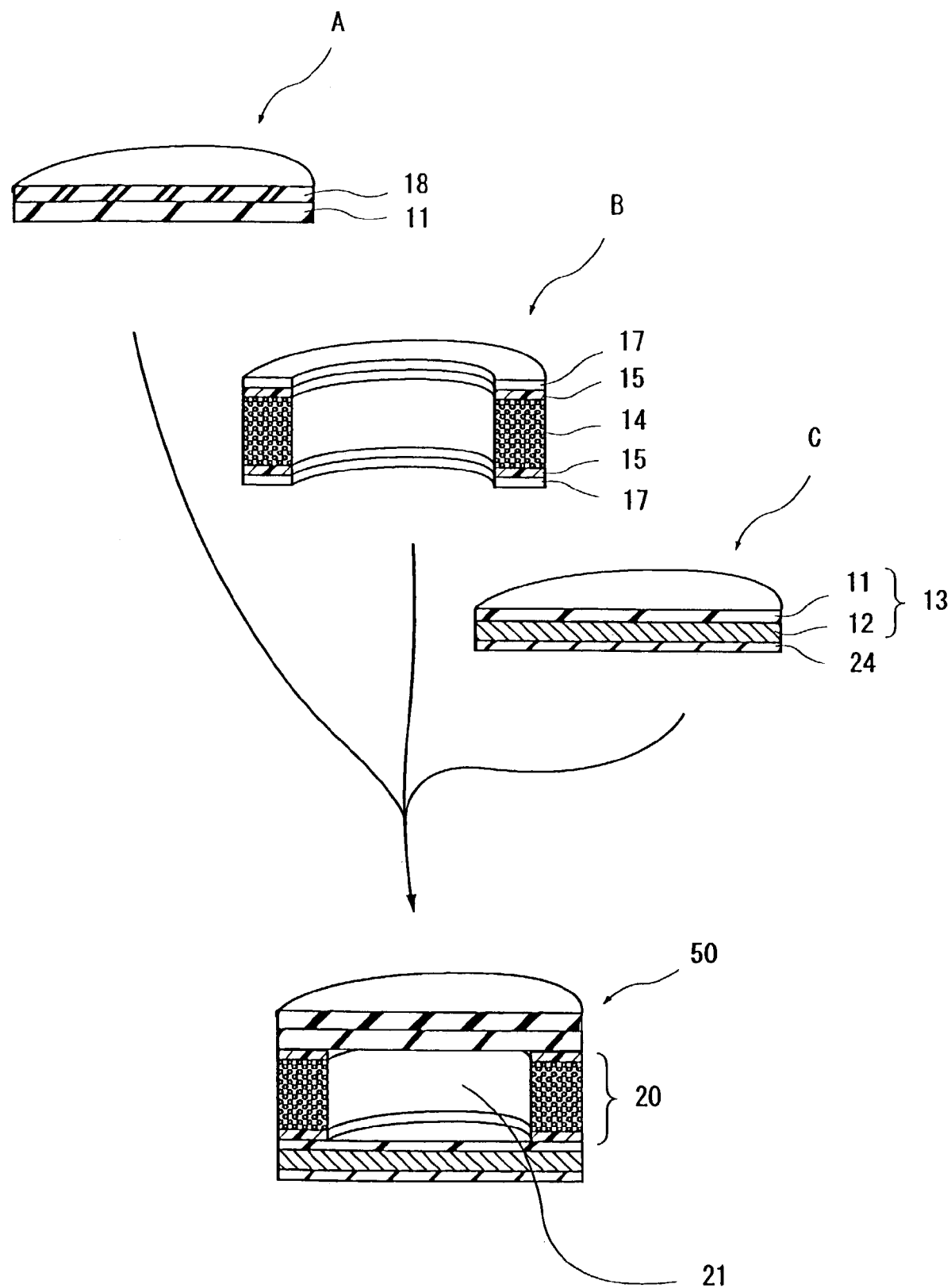
FIG. 4 is a view for explaining a manufacturing method of a percutaneous absorption system.
Figure 5:
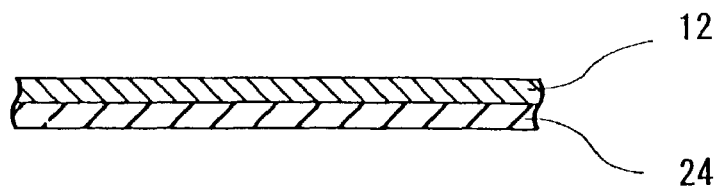
FIGS. 5(a)-5(d) are views for explaining the manufacturing method of the percutaneous absorption system.
Figure 5:
Figure 5:
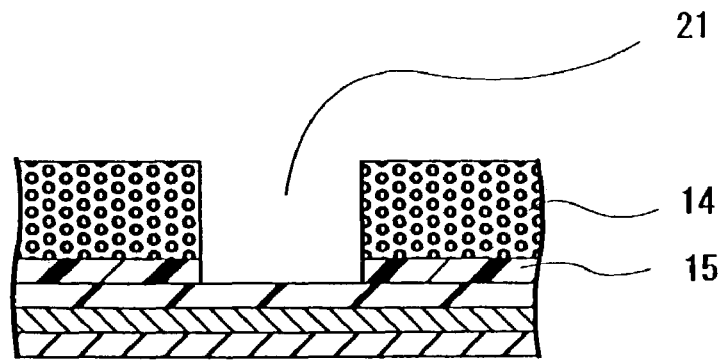
Figure 5:
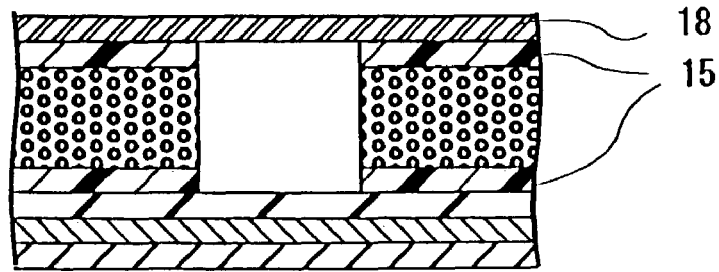
Figure 6:
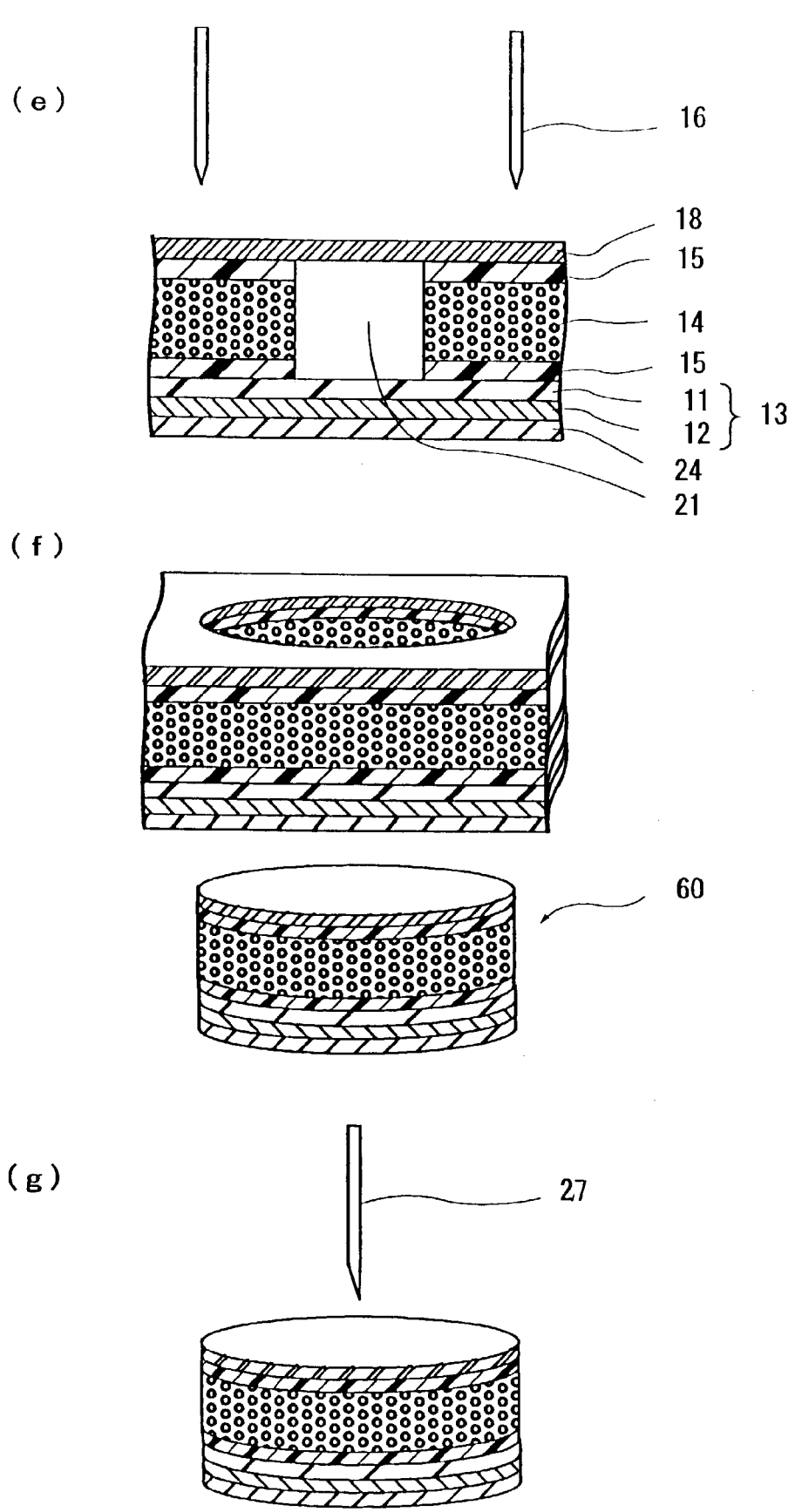
FIGS. 6(e)-6(g) are views for explaining the manufacturing method of the percutaneous absorption system.

Accordingly, it is preferable that the support portion 13 has a rectangular planar shape as shown in FIG. 1 to FIG. 3 or a shape corresponding to the cylindrical medicine reservoir portion 20 as shown in FIG. 4 to FIG. 6.

On the other hand, when a thickness of the support portion 13 is excessively increased, handling of the support portion 13 at the time of adhering the support portion 13 to a skin or the like becomes difficult and there may be a case that the support portion 13 is liable to be easily peeled off. Accordingly, as shown in FIG. 1 or the like, it is preferable to adopt a thin film shape as a cross-sectional shape of the support portion 13.

(2) Substrate Having Medicine Non-permeating Property (i) Type

Further, the type of the substrate having medicine non-permeating property in the support portion is not specifically restricted. However, it is preferable to use a plastic film such as a polyester film, a polyamide film, polyolefin film, a poly-styrene film, a polyvinyl chloride film, a fluororesin film, a polycarbonate film, a polysulfone film, polyimide film, a silicone resin film or the like.

The reason is that with the use of this type of substrate, the support portion can have the proper mechanical strength and durability and hence, even when the pressure is applied to the medicine, there is a small possibility that the medicine comes out from the substrate or the substrate is excessively deformed.

Further, provided this type of substrate is adopted, since the substrate can have the proper rupture strength and hence, the substrate can be easily broken by the mechanical stimulus such as the injection needle. Further, with use of such a substrate, it is possible to respectively laminate the medicine reservoir portion and the adhesive layer to both surfaces of the substrate so that the manufacture of the percutaneous absorption system can be extremely facilitated.

Here, the medicine non-permeating property of the substrate implies that there is no remarkable leaking of the medicine in a liquid form under the pressure applying condition, which will be explained later.

(ii) Thickness

Further, it is preferable that a thickness of the substrate having medicine non-permeating property in the support portion is set to a value, which falls within a range of about 5 to 1000 μm.

The reason is that when the thickness of the substrate having medicine non-permeating property assumes a value below 5 μm, there may be a case that it is difficult for the support portion to support the medicine reservoir portion or it is difficult to laminate the adhesive layer. On the other hand, when the thickness of the substrate exceeds 1000 μm, it may be difficult to adhere the support portion to a skin or the like following an irregular surface of the skin or the like or it may be difficult to easily break the substrate using the mechanical stimulus such as an injection needle.

Accordingly, it is more preferable to set the thickness of the substrate having the medicine non-permeating property in the support portion to a value, which falls within a range of about 10 to 100 μm. It is further more preferable to set the thickness of the substrate having the medicine non-permeating property in the support portion to a value, which falls within a range of about 15 to 50 μm.

(iii) Breaking Portion

Figure 8:
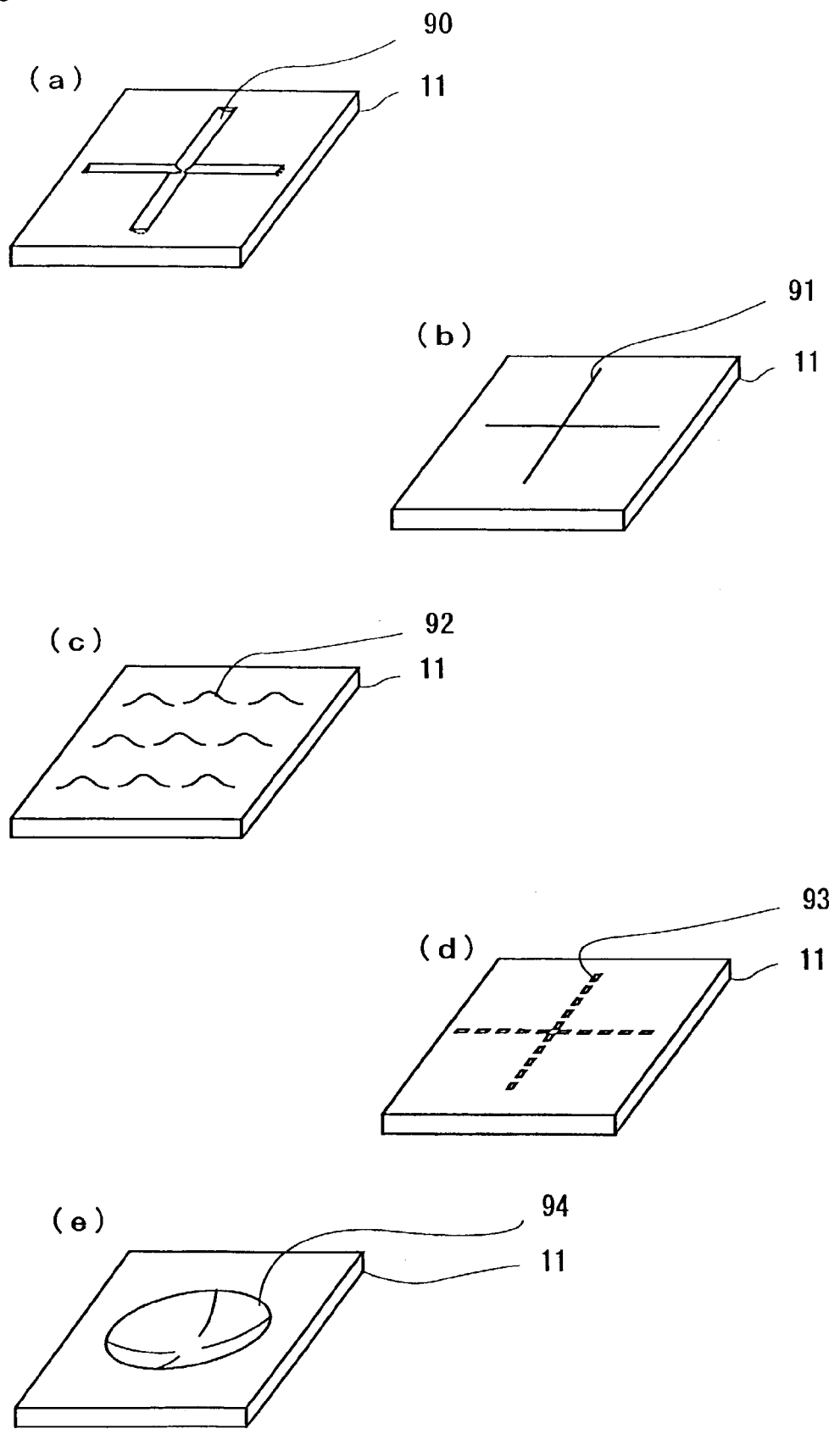
FIGS. 8(a)-8(e) are views for explaining the structure of a substrate.

Further, it is preferable to form at least one breaking portion such as a slit 90 shown in FIG. 8 (a), a score line 91 shown in FIG. 8 (b), an emboss 92 shown in FIG. 8 (c), a sawing stitch 93 shown in FIG. 8 (d) or a thin wall portion 94 shown in FIG. 8 (e) or the like.

The reason is that by providing such a breaking portion, even when the substrate is formed of a material which is originally difficult to break, the substrate can be easily broken using the mechanical stimulus such as an injection needle or the like and it is possible to effectively prevent the breaking of the substrate at portions thereof other than given portions.

Here, to prevent the breaking of the substrate and leaking of medicine even in a state that the pressure is applied to the medicine, when the slit 90 shown in FIG. 8 (a), the score line 91 shown in FIG. 8 (b), the emboss 92 shown in FIG. 8 (c) or the sawing stitch 93 shown in FIG. 8 (d) is formed, it is preferable to form such a breaking portion in the vicinity of a center portion of the substrate. Further, in such a breaking portion, it is preferable that the breaking portion does not penetrate the substrate having medicine non-permeating property in the thicknesswise direction until a mechanical stimulus such as an injection needle or the like is given.

(iv) Transparency and the Like

Further, it is preferable that the substrate having medicine non-permeating property in the support portion is transparent or semitransparent. Due to such a constitution, it is possible to observe a condition of a skin or the like through the substrate with naked eyes and hence, it is possible to accurately break a given portion even with the use of mechanical stimulus from the outside such as an injection needle.

Here, it is not always necessary that the substrate per se in the support portion have transparency or semi-transparency. That is, it is sufficient that an opening portion (window portion) or a slit is formed in a portion of the substrate in the support portion so that a skin or the like can be recognized as a background.

(v) Arrangement

Here, the substrate having medicine non-permeating property may be provided at least on the support portion. However, besides such an arrangement, it is preferable to provide the substrate 11 having medicine non-permeating property not only to the support portion 13 but also to a ceiling portion of the medicine reservoir portion 20. In this case, although it is necessary to break the substrate at least at two portions, the deformation of the substrate can be further reduced correspondingly even when the pressure is applied and hence, leaking of the medicine before use can be sufficiently prevented. Further, by providing the substrate having medicine non-permeating property to the ceiling portion, the substrate also performs a function of a substrate when a liquid leaking preventing layer is formed. Accordingly, it is possible to easily provide the liquid leaking preventing layer having a uniform thickness.

Further, as shown in FIGS. 2 (a) and (b), it is preferable that the substrate 11 of the support portion is extended to form a portion or the whole of the sidewall of the medicine reservoir portion. Due to such a constitution, even when the pressure is applied, it is possible to reduce the deformation of the medicine reservoir portion so that leaking of medicine in a liquid form before use can be sufficiently prevented.

Further, as shown in FIG. 3 (a), it is also preferable to provide the substantially integral type structure formed of the substrate 11 having medicine non-permeating property by providing the substrate 11 having medicine non-permeating property to not only the support portion 13 but also to the sidewall and the ceiling portion of the medicine reservoir portion 20. Further, as shown in FIG. 3 (a), by laminating an elastic member to a portion of the sidewall formed of medicine non-permeating property, it is possible to efficiently apply pressure to the medicine and leaking of medicine before use can be prevented.

Here, as shown in FIG. 3 (a), when the whole of the medicine reservoir portion 20 is formed of the substrate having medicine non-permeating property, it is also preferable that a cap-like member which corresponds to the sidewall and the ceiling portion of the medicine reservoir portion 20 is preliminarily prepared and the cap-like member is laminated to a film formed of the substrate having medicine non-permeating property in a state that the elastic member is filled in the cap-like member. Due to such a constitution, even when the pressure is applied to the medicine, it is possible to sufficiently prevent leaking of the medicine and the percutaneous absorption system can be manufactured extremely easily.

(3) Adhesive Layer (i) Type

Although a type of an adhesive agent which constitutes the adhesive layer in the support portion is not specifically limited, an acrylic pressure sensitive adhesive, a silicone-based pressure sensitive adhesive, a rubber-based pressure sensitive adhesive or the like, for example, can be named.

Further, to surely support the medicine reservoir portion containing the medicine under pressure, it is preferable to set a glass transition temperature of these pressure sensitive adhesives obtained by the DSC measurement to a value which falls within a range of about $-40$ to $-10°$ C.

Further, at the time of using the percutaneous absorption system by adhering the percutaneous absorption system in a state that the medicine reservoir portion which has the medicine holding portion is surely supported, it is preferable that the pressure sensitive adhesive has given creep resistance so as to prevent the displacement. For example, when the acrylic pressure sensitive adhesive is used, it is preferable to provide a partial crosslinking using a urea compound or an isocyanate compound. Further, when the silicone-based pressure sensitive adhesive is used, it is preferable to provide partial cross inking using a platinum catalyst. Further, when the rubber-based pressure sensitive agent is used, to obtain given creep resistance, it is preferable to use the rubber-based pressure sensitive adhesive in a state that thermoplastic elastomer such as SBS resin, SIS resin or the like having the excellent creep resistance is used as a rubber component or a self-crosslinking component is mixed into the rubber component.

(ii) Arrangement and Thickness

Further, with respect to the arrangement of the adhesive layer 12 in the support portion 13, as shown in FIGS. 1 (a) and (b), the adhesive layer 12 may be provided to a whole surface of the medicine non-permeating layer 11 or to a portion of the medicine non-permeating layer 11. Here, even when the adhesive layer 12 is provided to the whole surface of the medicine non-permeating layer 11, it is preferable that the medicine non-permeating layer 11 can be easily broken by the mechanical stimulus such as an injection needle or the like.

Further, it is preferable to set a thickness of the adhesive layer in the support portion to a value, which falls within a range of about 5 to 1000 μm.

The reason is that when the thickness of the adhesive layer assumes a value below 5 μm, there may be a case that it is difficult to support the medicine reservoir portion or to laminate the adhesive layer uniformly. On the other hand, when the thickness of the adhesive layer exceeds 1000 μm, it may be difficult to adhere the support portion to a skin etc. following an irregular surface of the skin etc. or it may be difficult to easily break the substrate using the mechanical stimulus such as an injection needle or the like. Further, when the thickness of the adhesive layer exceeds 1000 μm, there may be a case that it is difficult to make the medicine permeate the adhesive layer.

Accordingly, it is more preferable to set the thickness of the adhesive layer to a value, which falls within a range of about 10 to 100 μm. It is further more preferable to set the thickness of the adhesive layer to a value, which falls within a range of about 15 to 50 μm.

(iii) Transparency and the Like

Further, it is preferable that the adhesive layer in the support portion is transparent or semitransparent. Due to such a constitution, it is possible to observe a condition of a skin or the like which constitutes a subject to be adhered through the adhesive layer and the substrate having medicine non-permeating property with naked eyes. That is, it is possible to accurately and easily break the adhesive layer together with the substrate with the use of a mechanical stimulus from the outside such as an injection needle, for example, after recognizing the adhesive layer in the support portion.

Here, in the same manner as the substrate having medicine non-permeating property, it is not always necessary that the adhesive layer per se have transparency or semi-transparency. For example, it is sufficient that the adhesive layer is formed in an island shape or a line shape thus forming a non-coated portion or an opening portion at portions of the neighboring adhesive layer so that a skin or the like can be recognized as a background.

3. Elastic Member

The elastic member for applying pressure to the medicine by way of the medicine holding portion constitutes, as shown in FIG. 1, a portion or the whole of the medicine reservoir portion 20 and is served for applying pressure to the medicine 19 by making use of a return deformation force of the elastic member. That is, it is preferable that the medicine reservoir portion 20 includes the medicine holding portion 21 which defines a space for holding the medicine 19 in the inside thereof and forms sidewalls or the like which has the circular or the rectangular planar shape and is constituted of the elastic member, and uses the elastic member as the pressure applying means.

As such an elastic member, a rubber plate which is formed of silicone rubber, natural rubber, chloroprene rubber, isoprene rubber, EVA, SBS, SIS, SEBS, NBR rubber or the like can be preferably used. With the use of such a rubber plate, the elastic member is suitably elongated and shrunken upon applying of pressure so that it is possible to deliver the medicine at a fixed rate.

Further, it is also preferable to use the elastic member, which is formed of a foamed body such as a polyethylene-foamed body, a styrene foamed body or the like. The reason is that with the use of such a foamed body, even when the medicine is filled in the inside of the medicine holding portion and the pressure is applied to the medicine, the elastic member can easily maintain a fixed shape. Further, with the use of such a foamed body, it is possible to apply the appropriate pressure to whole medicine and it is possible to deliver the medicine at a fixed rate accurately at the time of use of the percutaneous absorption system. Further, when the elastic member is formed of such a foamed body, it is possible to easily manufacture at least the sidewall by die cutting or the like.

Here, to effectively make use of the return deformation force of the elastic member, assuming a volume of the medicine holding portion as 100 volume %, it is preferable to set a quantity of the medicine (medicine in a liquid form) to be filled in the medicine holding portion to a value which falls within a range of about 110 to 300 volume %.

4. Mechanical Stimulus (1) Mechanical Stimulus Given from the Outside

In the percutaneous absorption system, as shown in FIG. 1(b) and FIG. 3(b), the mechanical stimulus for breaking the substrate 11 having medicine non-permeating property in the support portion 13, that is, the breaking means is preferably the breaking means 26 which is given from the outside of the percutaneous absorption system. The reason is that, due to such a constitution, the percutaneous absorption system can have the simple constitution and the percutaneous absorption system can exhibit the excellent portability at the time of storing the system compared to a constitution explained later in which a projection is provided in the inside of the medicine reservoir portion.

Further, such a breaking means 26 may be preferably a needle-like member of a given size which can penetrate a portion of a skin after passing the substrate 11 having medicine non-permeating property of the support portion 13 and can allow the medicine to be gradually delivered without generating leaking of the medicine after the breaking means 26 is removed. As such breaking means, it is preferable to use at least one of an injection needle (injector), a pin, a thumb tack, a needle for sawing, a needle of a stapler, a wire, a knife or the like, for example. Further, it is also possible to use a non-needle injection such as a jet injector or the like.

When the injection needle (injector) is used, as preferable examples, a stainless steel injection needle which satisfies the standard 25 G (outer diameter: 0.45 mm) and a stainless steel needle (diameter: 0.26 mm, length: 1.55 mm) are named.

Here, the inventors have found that the delivery speed of the medicine is remarkably changed in response to a physical magnitude of the mechanical stimulus, for example, the diameter of the injection needle. Accordingly, it is preferable to determine the physical magnitude of the mechanical stimulus based on a calculation, which uses the optimal delivery speed of the medicine.

(2) Mechanical Stimulus Given from the Inside (i) Constitution

Further, in the percutaneous absorption system, as shown in FIG. 9(b), it is also preferable that the mechanical stimulus for breaking the substrate 11 having medicine non-permeating property in the support portion 13 is the mechanical stimulus due to a projection 5 provided in the inside of the percutaneous absorption system. That is, the mechanical stimulus is obtained by the projection 5 which is provided in the inside of the medicine reservoir portion 20 for breaking the substrate 11 having medicine non-permeating property of the support portion 13. The reason is that, due to such a constitution, it is unnecessary to prepare other breaking means at the time of using the percutaneous absorption system. Accordingly, the percutaneous absorption system is not restricted by a using condition and its usage becomes really easy.

Further, such a projection 5 may preferably be a needle-like member of a given size which can penetrate a skin (not shown in the drawing) after passing the substrate 11 having medicine non-permeating property of the support portion 13 and can allow the medicine to be gradually delivered without generating leaking of the medicine after the projection 5 is removed. Accordingly, although the configuration of the projection is not specifically restricted, it is preferable to use a needle-like member such as an injection needle (injector), a pin, a thumb tack, a needle for sawing, a needle of a stapler, a wire, a knife or the like.

Further, when the needle-like member is used as the projection, it is preferable to set the diameter of the needle-like member to a value, which falls within a range of about 0.1 to 3 mm. Accordingly, when the injection needle is used, it is preferable to use an injection needle, which satisfies the standard such as 25 G or the like.

Figure 9:
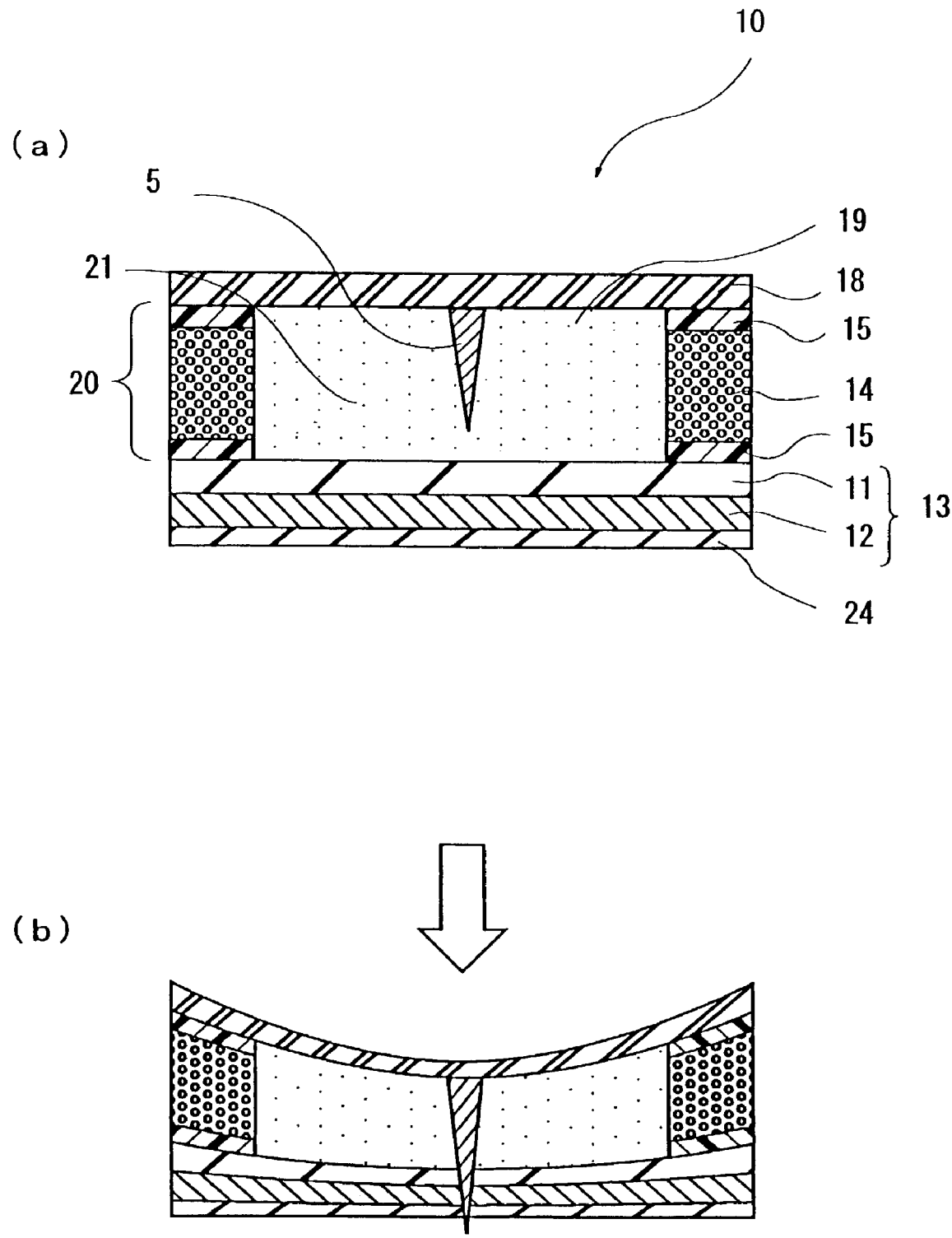
FIG. 9(a) is a view for explaining the structure of a percutaneous absorption system having a projection and using an elastic member and FIG. 9(b) is a view for explaining a state in which the projection is used.

Further, as shown in FIG. 9, it is preferable to form the projection into a cone shape. Due to such a constitution, it is possible to easily break the substrate having medicine non-permeating property and the like with a distal end thereof and it is possible to firmly mount the projection in the inside of the medicine reservoir portion by making use of a proximal portion of the projection having a relatively large area.

Further, it is preferable to set a length of the projection to a value, which falls within a range of about 0.5 to 20 mm. The reason is that when the length of the projection is below 0.5 mm, there may be a case that it is difficult to break the substrate having medicine non-permeating property, while when the length of the projection exceeds 20 mm, the medicine reservoir portion to which the projection is mounted has to be increased in size correspondingly.

Accordingly, it is more preferable to set the length of the projection to a value, which falls within a range of about 1 to 10 mm, and it is further more preferable to set the length of the projection to a value, which falls within a range of about 2 to 8 mm.

Figure 10:
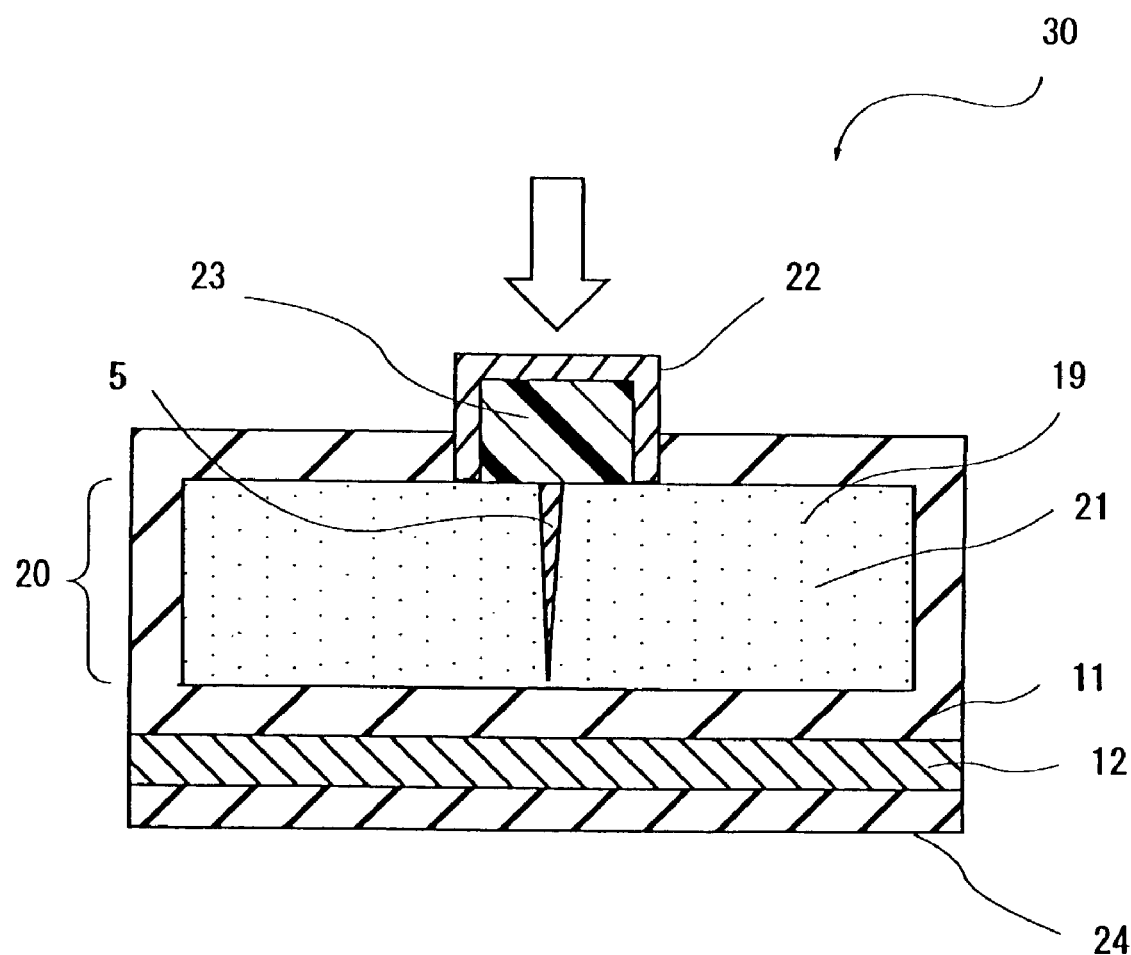
FIG. 10 is a view for explaining the structure of a percutaneous absorption system having a projection, wherein the system includes another pressure applying member.
Figure 11:
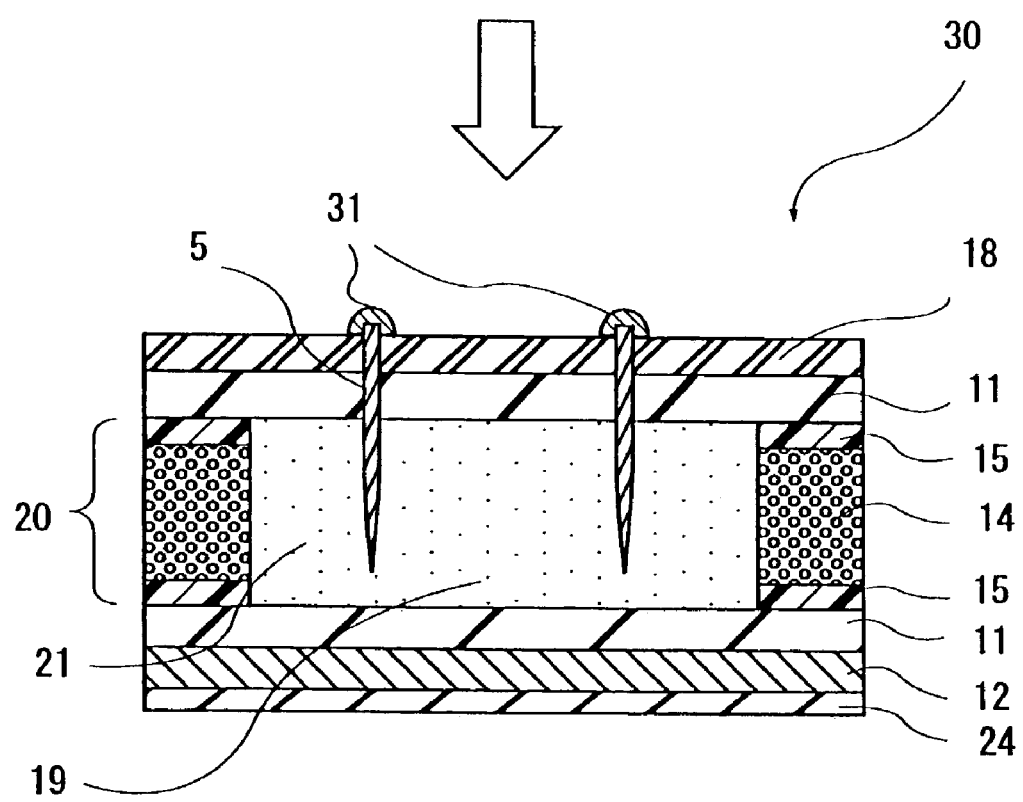
FIG. 11 is a view for explaining the structure of a percutaneous absorption system having a plurality of projections.

Further, as shown in FIG. 10 and FIG. 11, it is preferable to provide a pushing portion to a proximal end portion of the projection 5 for pushing the projection 5 downwardly.

The reason is that, due to such a constitution, it is possible to easily grasp the position of the projection in the inside of the medicine reservoir portion and it is possible to push the projection via the pushing portion accurately with a slight force. Accordingly, the substrate having medicine non-permeating property can be broken easily and speedily.

Figure 12:
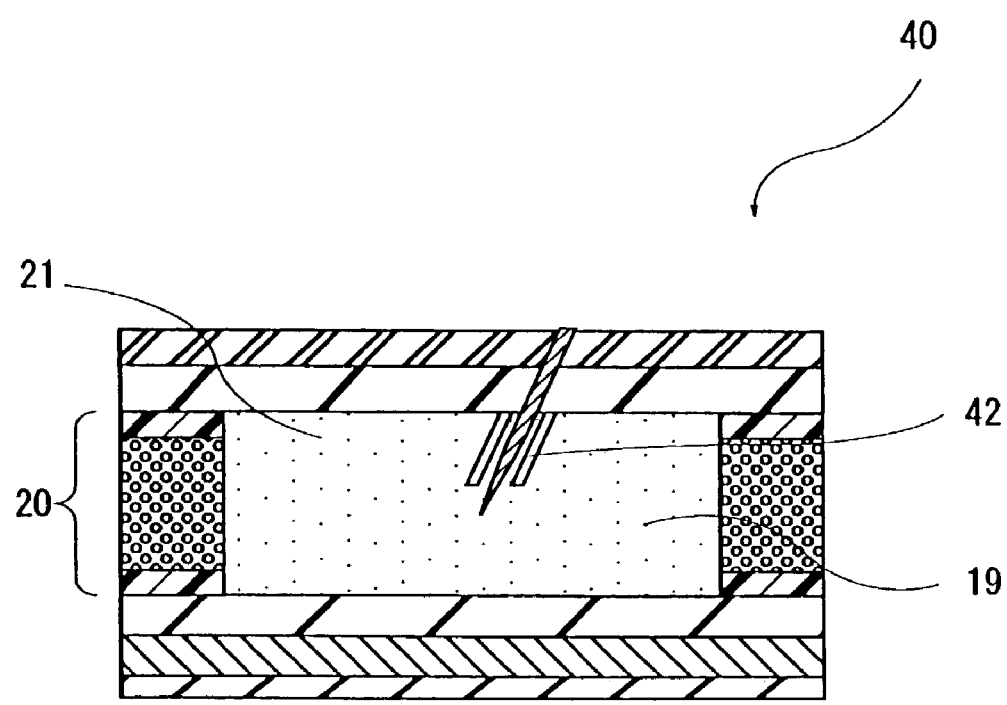
FIG. 12 is a view for explaining the structure of a percutaneous absorption system having a guide member for a projection.

Further, as shown in FIG. 12, it is preferable to provide a guide member 42 to the percutaneous absorption system for guiding the projection 5.

The reason is that it is possible to direct the projection in a fixed direction corresponding to an angle, which the guide member makes with respect to the substrate having medicine non-permeating property or a skin. That is, it is possible to suitably change an advancing angle of the projection corresponding to the angle of the guide member. For example, the projection can penetrate the skin in the direction, which makes about 45°, for example, with respect to the skin. Further, with the provision of the guide member, there is a little possibility that a pushing force given to the projection is dispersed whereby the substrate having medicine non-permeating property can be easily broken compared to the constitution which has no guide member.

Further, although the material of the guide member is not specifically restricted, it is preferable that the guide member is formed of plastic resin, ceramic resin, metal or the like, for example.

Here, as shown in FIG. 12, it is preferable that the distal end portion is set free so that even when the projection returns to the original position, the delivery of the medicine is not obstructed by the guide member.

(ii) Arrangement

Further, as shown in FIG. 9(a), it is preferable to arrange the projection 5 in a state that the distal end portion of the projection 5 extends downwardly and is perpendicular to the substrate 11 having medicine non-permeating property.

The reason is that, by arranging the projection in such a manner, the projection can easily penetrate into the inside of a skin, not to mention the substrate having medicine non-permeating property. Further, since the projection advances perpendicularly, it is also possible to withdraw the projection perpendicularly in the same manner after forming an opening or the like by the projection.

Further, as shown in FIG. 9(a) and FIG. 10 and the like, it is preferable that the projection 5 is formed on an upper surface of the medicine reservoir portion 20. The reason is that, due to such an arrangement of the projection 5, it is possible to increase a movable distance (stroke) of the projection and hence, the projection can easily penetrate the skin and reach an arbitrary position of the skin, not to mention the substrate having medicine non-permeating property. Here, since the projection 5 shown in FIG. 10 is arranged on the upper surface of the medicine reservoir portion 20 by way of the support member 13, it is possible to firmly mount the projection 5 and by covering the periphery of the projection 5 with a liquid leaking prevention member 22, it is possible to easily suppress leaking out of the medicine. Further, by arranging the projection 5 as shown in FIG. 10, it is possible to easily break at least the substrate 11 having medicine non-permeable property using the projection 5 by way of the support member 23.

Further, as shown in FIG. 11, it is also preferable to provide the projections 5 in a state that the projections 5 penetrate a liquid leaking preventing layer 18 formed on the upper surface of the medicine reservoir portion 20. Due to such a constitution, by simply pushing the liquid leaking preventing layer 18 from the outside of the medicine reservoir portion 20, the projections 5 can easily penetrate the skin, not to mention the substrate 11 having medicine non-permeating property. Further, due to such a constitution, the liquid leaking preventing layer 18 per se partially exhibits a force for supporting the projections 5 and hence, it is possible to reduce the size of the support member 31.

When the projection is made to be penetrated in an oblique direction with respect to a skin to reduce pain by taking QOL (Quality of Life) into account, it is preferable to provide the guide member as shown in FIG. 12.

(iii) Number of Projections

The number of projections is not specifically limited. Although it is preferable to determine the number of projections by taking the delivery speed of medicine into account, it is preferable to set the number of projections to a value of 1 to 10, for example.

The reason is that when the number of projections exceeds 10, there may be a case that the space for storing the medicine becomes excessively small and there may be a case that the manufacture of the percutaneous absorption system per se becomes difficult. Accordingly, it is more preferable to set the number of projections to a value, which falls within a range of 1 to 5, and it is further more preferable to set the number of projections to a value, which falls within a range of 1 to 3.

5. Liquid Leaking Preventing Layer

Further, in constituting the first percutaneous absorption system, it is preferable to provide the liquid leaking preventing layer on both of or either one of an inner surface and an outer surface of the medicine reservoir portion. That is, as illustrated in FIG. 1, in the percutaneous absorption system 10 which includes the medicine reservoir portion 20 and the support portion 13 including the adhesive layer 12 and the substrate 11 having medicine non-permeating property, it is preferable to provide the liquid leaking preventing layer 18 at an upper portion of the medicine reservoir portion 20.

The reason is that, with the provision of such a liquid leaking preventing layer, it is possible to effectively prevent the leaking of medicine (leaking of liquid) through the opening or the like formed by the mechanical stimulus in the midst of the operation to give the mechanical stimulus using the injection needle or the like or after such an operation.

Further, it is preferable that a thickness of the liquid leaking preventing layer is set to a value, which falls within a range of about 5 to 2000 μm. The reason is that when the thickness of the liquid leaking preventing layer assumes a value below 5 μm, there may be a case that a liquid leaking prevention effect is remarkably reduced or it is difficult to form the liquid leaking preventing layer having a uniform thickness. On the other hand, when the thickness of the liquid leaking preventing layer exceeds 2000 μm, there may be a case that the thickness of the percutaneous absorption system becomes excessively large and it takes a long time for forming the percutaneous absorption system.

Accordingly, it is more preferable to set the thickness of the liquid leaking preventing layer to a value, which falls within a range of about 50 to 1000 μm, and it is further more preferable to set the thickness of the liquid leaking preventing layer to a value, which falls within a range of about 100 to 500 μm.

Further, although the type of resin or the like which constitutes the liquid leaking preventing layer is not specifically limited, it is preferable that the liquid leaking preventing layer is constituted of silicone rubber, natural rubber, chloroprene rubber, isoprene rubber, NBR rubber or the like.

Here, although not shown in the drawing, before the percutaneous absorption system is used in a state that a peel-off film or the like is formed outside the liquid leaking preventing layer, it is preferable to protect the liquid leaking preventing layer using such a peel-off film or the like.

6. Manufacturing Method

Two examples of the manufacturing method of the percutaneous absorption system according to the first embodiment are explained in conjunction with FIG. 4 to FIG. 6 respectively. It is needless to say, however, that the present invention is not restricted to the manufacturing method described hereinafter and the manufacturing method can be suitably modified.

(1) Manufacturing Method 1

The manufacturing method 1 shown in FIG. 4 is a method in which respective constitutional members of the percutaneous absorption system are preliminarily prepared and these constitutional members are joined so as to manufacture the percutaneous absorption system 50 including the cylindrical elastic member 14 efficiently in a short time. This percutaneous absorption system 50 is an example in which the adhesive layers 15 (first adhesive layer and second adhesive layer from below) are formed on the upper and lower surfaces of the medicine reservoir portion 20, and two substrates 11 having medicine non-permeating property (first substrate having medicine non-permeating property and second substrate having medicine non-permeating property from below) are provided by way of these adhesive layers 15.

(i) Preparation of "A" Member

First of all, an "A" member which is provided with the liquid leaking preventing layer 18 formed of silicone rubber or the like on the second substrate 11 having medicine non-permeating property is prepared. The reason that the substrate 11 having medicine non-permeating property is provided below the liquid leaking preventing layer 18 is that, due to such a constitution, it is possible to easily and uniformly form the liquid leaking preventing layer 18 on the medicine reservoir portion 20. Further, although not shown in the drawing, it is also preferable to provide a peel-off film to the outside of the liquid leaking preventing layer 18 to protect the liquid leaking preventing layer 18. Here, in view of manufacturing of the cylindrical percutaneous absorption system, it is preferable to preliminarily cut the "A" member in a circular shape.

(ii) Preparation of "B" Member

Then, a "B" member, which is constituted of the cylindrical elastic member 14 and the first and second adhesive layers 15, which are formed on upper and lower surfaces of the elastic member 14, is prepared.

In this case, as shown in FIG. 4, it is preferable to provide peel-off films 17 to respective outsides of the upper-side and lower-side adhesive layers 15 to facilitate the handling of the "B" member.

(iii) Preparation of "C" Member

Further, a "C" member formed of the support portion 13 which is constituted of the substrate 11 having medicine non-permeating property and the adhesive layer 12 is prepared. Also with respect to the "C" member, as shown in FIG. 4, it is preferable to provide a peel-off film 24 to the outside of the adhesive layer 12 to facilitate the handling of the "C" member.

(iv) Lamination and Pressure Applying Treatment of "A" to "C" Members

Subsequently, after peeling off the peel-off film 17 which is formed on the upper surface of the "B" member, as shown by an arrow in FIG. 4, the second substrate 11 having medicine non-permeating property which is provided with the liquid leaking preventing layer 18 is laminated to the upper surface of the cylindrical elastic member 14 by means of the second adhesive layer 15.

In the same manner, after peeling off the peel-off film 17 which is formed on the lower surface of the "B" member, as shown by an arrow in FIG. 4, the first substrate 11 having medicine non-permeating property in the support portion 13 which is provided with the peel-off film 24 is laminated to the lower surface of the cylindrical elastic member 14 in the "B" member by means of the first adhesive layer 15.

Finally, although not shown in the drawing, as the pressure applying treatment, as an example, a quantity of medicine 19 which is not below an inner volume of the medicine holding portion 21 is filled in the medicine holding portion 21 by an injector by way of the liquid leaking preventing layer 18 thus manufacturing the percutaneous absorption system 50 which generates an inner pressure inside the medicine holding portion 21.

Due to such a manufacturing method, even when the type and the thickness of the pressure sensitive adhesive are changed, it is possible to easily and efficiently manufacture a desired percutaneous absorption system.

(2) Manufacturing Method 2

A manufacturing method 2 shown in FIG. 5 and FIG. 6 is a method, which efficiently manufactures the percutaneous absorption system 60 sequentially in the order from the lower support portion. For example, the manufacturing method 2 is a method, which is suitable for manufacturing the percutaneous absorption system having the cylindrical member efficiently and on a mass production basis. Here, also in this manufacturing method 2, assumed is a case in which the adhesive layers 15 (first adhesive layer and second adhesive layer from below) are formed on the upper and lower surfaces of the medicine holding portion 21, and a percutaneous absorption system 60 which is provided with the first substrate 11 having medicine non-permeating property is manufactured by way of these adhesive layers 15.

(i) Preparation of Support Portion

First of all, as shown in FIG. 5(a), the adhesive layer 12 having the peel-off film 24 is prepared. The adhesive layer 12 can be formed using a usual coating method, a printing method or the like.

Subsequently, as shown in FIG. 5(b), the first substrate 11 having medicine non-permeating property is laminated to the formed adhesive layer 12 so as to form the support portion. In this case, it is preferable to laminate the first substrate 11 having medicine non-permeating property by making use of the adhesive layer 12.

(ii) Preparation of Medicine Reservoir Portion

Subsequently, as shown in FIG. 5(c), the elastic member 14 which is expected to constitute the sidewall of the medicine reservoir portion later is laminated to one surface of the substrate 11 having medicine non-permeating property using the first adhesive layer 15. It is preferable to laminate such an elastic member 14 by a lamination method, for example.

Then, a portion in the elastic member 14 of the percutaneous absorption system which corresponds to a space which constitutes the medicine holding portion 21 is cut out or bored by a cutter or the like thus forming the medicine reservoir portion.

(iii) Preparation of Liquid Leaking Preventing Layer

Subsequently, as shown in FIG. 5(d), the second adhesive layer 15 is formed on the surface of the elastic member 14 and, thereafter, the liquid leaking preventing layer 18 is laminated to the whole elastic member 14.

(iv) Preparation of Percutaneous Absorption System

Then, as shown in FIG. 6(e) and FIG. 6(f), a portion of a contour of the percutaneous absorption system is cut out or bored by a cutter 16, for example. In this case, although it is preferable to cut out or bore the portion by making use of a shearing force of the cutter or the like, it is also preferable to cut out or bore the portion by making use of a laser, a water jet ejection or the like.

Finally, as shown in FIG. 6(g), as the pressure applying treatment, a quantity of medicine which is not below an inner volume of the medicine holding portion 21 is filled in the medicine holding portion 21 by an injection needle (injector) 27 as an example of breaking means 26 by way of the liquid leaking preventing layer 18 thus manufacturing the percutaneous absorption system 60 which generates an inner pressure inside the medicine holding portion 21.

By carrying out the above-mentioned steps, the manufacturing of the percutaneous absorption system 60 can be automated so that the percutaneous absorption system 60 having a given size can be efficiently manufactured based on a flow production.

Second Embodiment

The second embodiment is directed, as illustrated in FIG. 2, to a percutaneous absorption system 30 which includes a medicine reservoir portion 20 having a medicine holding portion 21 which holds medicine 19 therein and a support portion 13 for supporting the medicine reservoir portion 20 which is comprised of an adhesive layer (first adhesive layer) 12 and a substrate 11 having medicine non-permeating property (first substrate having medicine non-permeating property), wherein bubbles 32 which apply pressure to the medicine 19 held in the medicine holding portion 21 are introduced into the inside of the medicine holding portion 21 and the substrate 11 having medicine non-permeating property in the support portion 13 is breakable upon receiving a mechanical stimulus.

Here, with respect to the detail of the mode of the medicine reservoir portion, the support portion, the mechanical stimulus, the liquid leaking preventing layer and the manufacturing method according to the second embodiment, they are substantially equal to those of the first embodiment. Accordingly, hereinafter, a point of the second embodiment, which is different from the first embodiment, that is, the bubbles introduced as the pressure applying means is explained in detail.

That is, the percutaneous absorption system of the second embodiment is directed, as illustrated in FIG. 2(a), to a system in which gas (compressed air or the like) is filled in the inside of the medicine holding portion and is allowed to be present in a form of bubbles thus applying pressure to the medicine 19. Further, as shown in FIG. 2(b), the gas is filled in the medicine holding portion 21 in which the medicine 19 is held by making use of the injection needle 27 by way of the liquid leaking preventing layer and the gas is allowed to be present in a form of bubbles.

Figure 13:
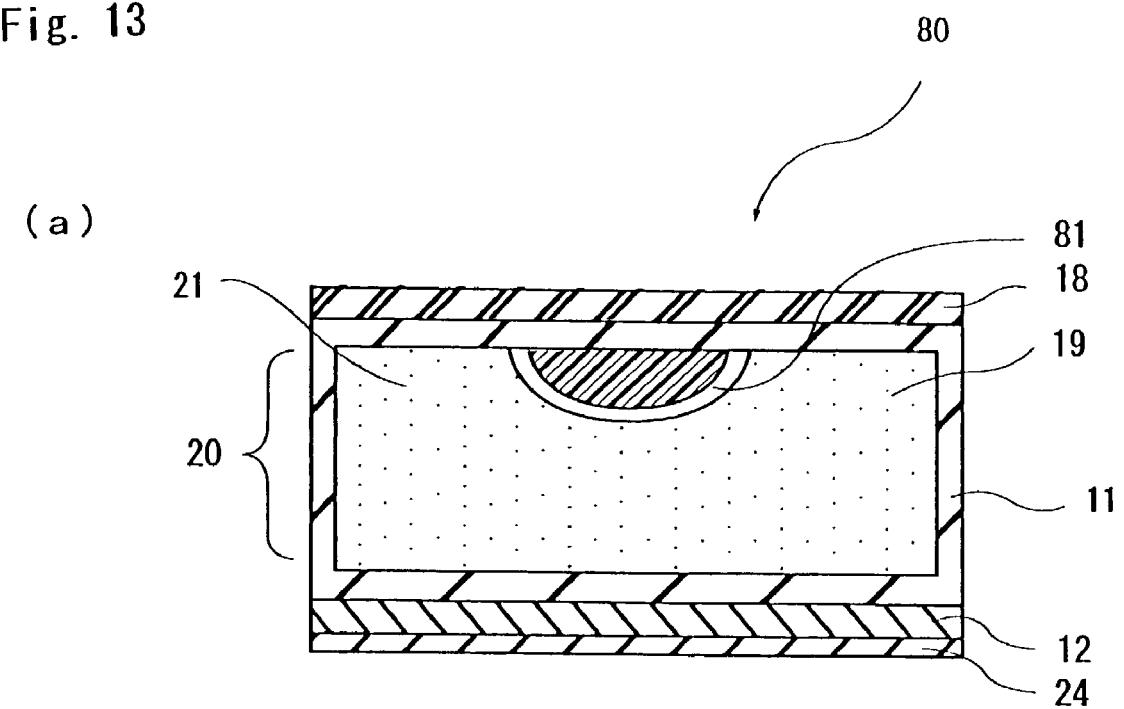
FIGS. 13(a) and 13(b) are views for explaining the structure of a percutaneous absorption system having a bulging portion.
Figure 13:
Figure 13:
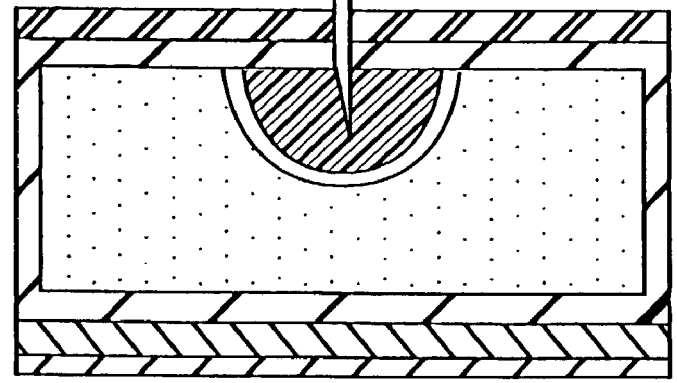

Further, it is also preferable that, as shown in FIG. 13(a), a bulging portion 81 such as a balloon whose volume is swelled is formed on the medicine reservoir portion 20 and, as shown in FIG. 13(b), gas is filled in the bulging portion 81 so as to expand the bulging portion 81 thus indirectly applying pressure to the medicine 19.

The reason is that, due to such a constitution, the gas and the medicine are completely separated and hence, it is possible to effectively prevent a portion of the bubbles from being dissolved in the medicine. Further, due to such a constitution, when the inner pressure of the medicine holding portion 21 is reduced due to the delivery of the medicine, it is possible to inject the gas again into the bulging portion 81 so as to restore the inner pressure to the initial pressure.

Further, along with the introduction of the bubbles into the medicine holding portion 21, it is also preferable that a portion or the whole of the medicine reservoir portion is constituted of the elastic member in the same manner as the first embodiment. The reason is that, due to such a constitution, it is possible to more reliably apply pressure to the medicine so that the delivery of the medicine is promoted.

Third Embodiment

The third embodiment is directed to a percutaneous absorption method which uses a percutaneous absorption system comprising a medicine reservoir portion having a medicine holding portion which holds medicine therein and a support portion for supporting the medicine reservoir portion, the support portion consisting of an adhesive layer and a substrate having medicine non-permeating property, wherein the method comprises following steps.

(1) A step for mounting the percutaneous absorption system (hereinafter also referred to as a mounting step), (2) A step for breaking at least the substrate having medicine non-permeating property in the support portion using a mechanical stimulus (also referred to as a breaking step), and (3) A step for delivering the medicine by applying pressure to the medicine using an elastic member provided to the medicine reservoir portion.

1. Mounting Step

This step is a step for adhering the percutaneous absorption system to a portion where it is necessary to percutaneously absorb medicine. It is preferable that the peel-off member, which is adhered to the adhesive layer, is peeled off and the percutaneous absorption system is adhered using a bare hand or a jig such as a pincette or the like. Further, it is also preferable that the percutaneous absorption system is automatically or semi-automatically adhered using a dedicated adhering jig.

Since the constitution or the like of the percutaneous absorption system to be adhered here can have the constitution substantially equal to the constitution, which has been explained in the first embodiment, and the second embodiment, the explanation of such a percutaneous absorption system is omitted here.

2. Breaking Step

This step is a process for breaking at least the substrate having medicine non-permeating property of the support portion using a mechanical stimulus.

That is, in this step, the substrate having medicine non-permeating property of the support portion is broken by giving the mechanical stimulus from the outside using an injection needle (injector) or the like or by giving the mechanical stimulus attributed to the projection provided in the inside of the medicine holding portion, and thereafter, the skin is pierced thus facilitating the delivery of the medicine.

Here, when the mechanical stimulus is given, as shown in FIG. 1, it is preferable that the liquid leaking preventing layer 18 is formed on the periphery of the medicine reservoir portion 20. The reason is that it is possible not only to prevent leaking of liquid but also to reduce the excessive lowering of an inner pressure even after the substrate 11 having medicine non-permeating property of the support portion 13 is broken by way of the medicine reservoir portion 20 and then the breaking means is removed.

3. Step for Delivering Medicine

This step is a step for delivering the medicine by making use of the inner pressure of the percutaneous absorption system or the difference in concentration of the medicine. That is, the medicine is pressurized and delivered due to the return deformation force of the elastic member, which constitutes a portion, or the whole of the medicine reservoir portion and the delivered medicine is administered by permeating the skin.

Here, it is preferable that a permeating speed of the delivered medicine per unit area is usually set to a value, which falls in a range of about 0.1 to 1000 μg/cm$^2$/hr although the permeating speed depends on the type or the like of the medicine. The reason is that when the permeating speed of the delivered medicine per unit area assumes a value which is below 0.1 μg/cm$^2$/hr, there may be a case that it takes an excessively long time before the medicine obtains a given concentration, while when the permeating speed of the delivered medicine per unit area exceeds 1000 μg/cm$^2$/hr, the irregularities of the permeating speed of the medicine is increased.

Fourth Embodiment

The fourth embodiment is directed to a percutaneous absorption method which uses a percutaneous absorption system comprising a medicine reservoir portion having a medicine holding portion which holds medicine therein and a support portion for supporting the medicine reservoir portion, the support portion including an adhesive layer and a substrate having medicine non-permeating property, wherein the method comprises following steps.

(1) A step for mounting the percutaneous absorption system (hereinafter also referred to as a mounting step), (2) A step for breaking at least the substrate having medicine non-permeating property in the support portion using a mechanical stimulus (also referred to as a breaking step), and (3) A step for delivering the medicine by applying pressure to the medicine using bubbles introduced into the medicine reservoir portion.

Here, with respect to the steps (1), (2) of the fourth embodiment, these steps (1), (2) can have the substantially same contents as the contents of the steps (1), (2) of the third embodiment. Accordingly, the step (3) of the fourth embodiment, which constitutes a point for making the fourth embodiment different from the third embodiment, is specifically explained hereinafter.

That is, although the step for delivering the medicine in the fourth embodiment is also a step for delivering the medicine by making use of the inner pressure of the percutaneous absorption system, the difference in concentration or the like, in the fourth embodiment, the medicine is delivered by applying pressure to the medicine using the bubbles introduced into the medicine reservoir portion. Then, the delivered medicine is administered by permeating the skin.

Here, it is preferable that a permeating speed of the delivered medicine per unit area is usually set to a value, which falls in a range of about 1 to 1000 μg/cm$^2$/hr although the permeating speed depends on the type or the like of the medicine. The reason is that when the permeating speed of the delivered medicine per unit area assumes a value which is below 1 μg/cm$^2$/hr, there may be a case that it takes an excessively long time before the medicine obtains a given concentration, while when the permeating speed of the delivered medicine per unit area exceeds 1000 μg/cm$^2$/hr, the irregularities of the permeating speed of the medicine is increased.

Example

Although the percutaneous absorption system and the percutaneous absorption method according to the present invention are explained in detail hereinafter based on examples, it is needless to say that the present invention is not limited by the description of these examples.

Example 1

1. Preparation of Percutaneous Absorption System

The acrylic pressure sensitive adhesive which will have a thickness of 25 μm after drying is applied onto the peel-off film SP-PET3801 (manufactured by Lintec Corporation) having a film thickness of 38 μm and, thereafter, the acrylic pressure sensitive adhesive is dried for three minutes at 100° C. to form the adhesive layer. Further, the first substrate having non-permeating property (polyethylene terephthalate film having a film thickness of 17 μm) is laminated to the adhesive layer to form the support portion.

Then, the silicone pressure sensitive adhesives are applied by coating to both surfaces of a polyethylene-foamed body "PEF" (manufactured by Toray Corporation) which constitutes the elastic member as pressure applying means. Then, the silicone pressure sensitive adhesives are dried under given conditions, that is, at a temperature of 100° C. for three minutes thus respectively forming the adhesive layers (first adhesive layer and second adhesive layer) having a thickness of 15 μm respectively). The polyethylene-foamed body having the adhesive layers is laminated to the first substrate having medicine non-permeating property by way of the first adhesive layer. The silicone type pressure sensitive adhesive is prepared and used by adding two parts by weight of DX-3004 (made by Shinetsu Chemical Industries., Ltd.) which works as a catalyst, to 100 parts by weight of X-40-3068 (made by Shinetsu Chemical Industries., Ltd.) as a main polymer of the silicone type pressure sensitive adhesive.

Then, the space, which constitutes the medicine holding portion of the polyethylene-foamed body, is formed by cutting out or boring the polyethylene-foamed body thus forming the medicine reservoir portion. Here, the thickness and the height of the sidewall are set to 5 mm and 1.5 mm respectively.

Subsequently, a mixture (weight ratio 10:1) of silicone type resin "SILASTIC MDX4-4210 Elastomer Base" (made by Dow Corning Corporation) and a curing agent (made by Dow Corning Corporation) is applied to the peel-off film SP-PET 3801(manufactured by Lintec Corporation) by coating and the mixture is heated at a temperature of 100° C. for 7 minutes. The liquid leaking preventing layer which is a silicone film having a thickness of 250 μm is laminated to the polyethylene foamed body of the medicine reservoir portion by way of the second adhesive layer.

In this manner, a casing of the percutaneous absorption system 10 illustrated in FIG. 1 is formed. Here, the casing includes the peel-off film 24, the acrylic adhesive layer 12, the first substrate having medicine non-permeating property (PET film having a thickness of 17 μm) 11, the medicine holding portion 21 formed of the polyethylene foamed body 14, and the liquid leaking preventing layer 18 formed of the silicone film in the order from below.

Here, the acrylic pressure sensitive adhesive layer is prepared by adding hexamethylene di-ethylene urea as a crosslinking agent to an acrylic adhesive solution in a solution polymerization such that the hexamethylene di-ethylene urea amounts to 0.2 parts by weight with respect to 100 parts by weight of the acrylic pressure sensitive adhesive in a solid conversion. Further, the acrylic pressure sensitive solution is prepared such that, in a separable flask, to 100 parts by weight of a monomer mixed solution consisting of 65 parts by weight of acrylic acid-n-butyl, 32 parts by weight of acrylic acid-2-ethyhexyl and 3 parts by weight of acrylic acid, 50 parts by weight of ethyl acetate is further added and, thereafter, 0.25 parts by weight of azobisisobutyronitrile is added as a radical initiator, and further, 80 parts by weight of ethyl acetate is added under the polymerization condition that the polymerization is performed in the nitrogen atmosphere at a temperature of 65° C. for 12 hours.

Subsequently, in the medicine holding portion of the medicine reservoir portion, a FITC dextran aqueous solution (weight-average molecular weight: 4000) having a concentration of 0.5% by weight is filled by a quantity corresponding to 165% of an inner volume (100%) of the medicine holding portion using an injector by way of the liquid leaking preventing layer such that the FITC dextran aqueous solution receives an inner pressure from the polyethylene foamed body.

Here, although the inner wall of the polyethylene foamed body which constitutes the sidewall of the medicine reservoir portion is subjected to the expansion in volume toward the outside, the polyethylene foamed body absorbs such an expansion in volume in the course of expansion from the inner wall to the outer wall and hence, the expansion of the outer wall per se is not specifically observed. Then, the injector is removed by way of the liquid leaking preventing layer thus manufacturing a percutaneous absorption system for evaluation of the first example 1.

2. Evaluation In Vitro of Percutaneous Absorption System

A vertical diffusion cell is formed and a skin which is cut out from a hairless rat (WBN/ILA-Ht, weight: about 200 g, the same type rat being used hereinafter) is mounted on the vertical diffusion cell and the percutaneous absorption system shown in FIG. 1 from which the releasing film is removed, is adhered to a stratum corneum of the skin of the hairless rat.

Then, in a state that purified water of a temperature of 32° C. is inserted into a receptor of the vertical diffusion cell, the skin of the hairless rat is pierced and penetrated with a needle (26 G) through the liquid leaking preventing layer of the percutaneous absorption system. Then, after removing the injection needle from the liquid leaking preventing layer, a cumulative quantity (permeating quantity per unit area) of the FITC dextran which is permeated to the purified water in the receptor via the skin of the hairless rat, is measured.

Here, the quantitative analysis of the FITC dextran concentration in the purified water is performed using a fluorometric luminous intensity meter RF-5300PC (manufactured by Shimadzu Corporation). An obtained result is shown in Table 1 and FIG. 14.

From this obtained result, it is confirmed that the measured permeating quantity of FITC dextran and time are changed about in a straight line and the FITC dextran having a weight-average molecular weight of 4,000 is permeated at a fixed rate. Further, even after the injection needle is removed from the liquid leaking preventing layer, no leaking of the dextran aqueous solution is observed.

Example 2 and Example 3

Except for that the weight-average molecular weight of 4000 of the FITC dextran in the example 1 is changed to 20,000 in the example 2 and 40,000 in the example 3, the percutaneous absorption systems similar to that of the embodiment 1 are prepared in the embodiment 2 and the embodiment 3.

Then, in the same manner as the embodiment 1, using the vertical diffusion cell, a cumulative quantity (permeating quantity per unit) of FITC dextran, which is permeated through the skin of the hairless rat, is measured. Obtained results are respectively shown in Table 1 and FIG. 14.

From these results, in both of the example 2 and the example 3, it is observed that although respective measured concentrations per se are lowered possibly due to the increase of the weight-average molecular weights, the permeating quantity of FITC dextran and time are changed about in a straight line. Accordingly, it is confirmed that even when either one of the FITC dextran having a weight-average molecular weight of 20,000 and the FITC dextran having a weight-average molecular weight of 40,000 is adopted, the FITC dextran is permeated at a fixed rate.

Example 4

1. Preparation of Percutaneous Absorption System

In the example 4, a filled quantity of FITC dextran in the medicine reservoir portion in the percutaneous absorption system of the example 1 is set to 100% with respect to the inner volume (100%) of the medicine holding portion and the bubbles are filled in the medicine holding portion using an injector. Here, compressed air is filled in the medicine holding portion such that the volume of the polyethylene foamed body which constitutes the sidewall of the medicine reservoir portion is expanded by about 10% so that the inner pressure is applied to the FITC dextran aqueous solution. Subsequently, the injector is removed thus forming the percutaneous absorption system for evaluation of the example 4.

2. Evaluation of Percutaneous Absorption System

Then, in the same manner as the embodiment 1, using the vertical diffusion cell, a cumulative quantity (permeating quantity per unit) of FITC dextran, which is permeated through the stratum corneum of the hairless rat, is measured. Obtained results are respectively shown in Table 1 and FIG. 15.

From these results, in the example 4, it is observed that the concentration of FITC dextran and time are changed about in a straight line. Accordingly, it is confirmed that even when the bubbles are used for applying pressure to the FITC dextran, the FITC dextran having a weight-average molecular weight of 4,000 is permeated at a fixed rate.

Example 5

1. Preparation of Percutaneous Absorption System

Except for that the FITC dextran aqueous solution in the example 1 is replaced with an insulin (molecular weight: about 6,000) having the concentration of 10 U/mL, the percutaneous absorption system is prepared in the same manner as the example 1.

2. Evaluation of Percutaneous Absorption System in Vivo Skin Permeating Example The percutaneous absorption system from which the peel-off film is removed is adhered to an abdomen of the hairless rat which is under urethane anesthetization and a skin of a hairless rat is pierced with an injector needle (26 G) through the liquid leaking preventing layer of the percutaneous absorption system. Then, after removing the injection needle from the liquid leaking preventing layer, the concentration of insulin in the blood plasma of the hairless rat is time-sequentially measured by a enzyme assay method using an insulin concentration measuring kit "Insulin Dynapak" (made by Dynapot Corporation). The concentration of insulin in the blood plasma is 105 μU/mL after 1 hour, 182 μU/mL after 3 hours, and 182 μU/mL after 5 hours. From these results, it is confirmed that the insulin, which is an aqueous high-molecular medicine, can be also administered by permeating the insulin through the skin. Also in this case, after removing the injection needle from the liquid leaking preventing layer, no leaking of the insulin aqueous solution is observed.

Comparing Examples 1 and 2

In a comparing example 1, a percutaneous absorption system is prepared and evaluated in the same manner as the example 1 except for that in place of the medicine reservoir portion formed of the polyethylene foamed body in the example 1, a medicine reservoir portion which is wholly formed of a PET film is prepared and the medicine is filled in the medicine reservoir portion such that the medicine assumes 90% with respect to the inner volume (100%) of the liquid reservoir portion thus preventing the generation of the inner pressure in the medicine.

Further, in a comparing example 2, a percutaneous absorption system is prepared and evaluated in the same manner as the comparing example 1 except for that a mechanical stimulus by an injection needle in the comparing example 1 is not given in the comparing example 2.

Figure 14:
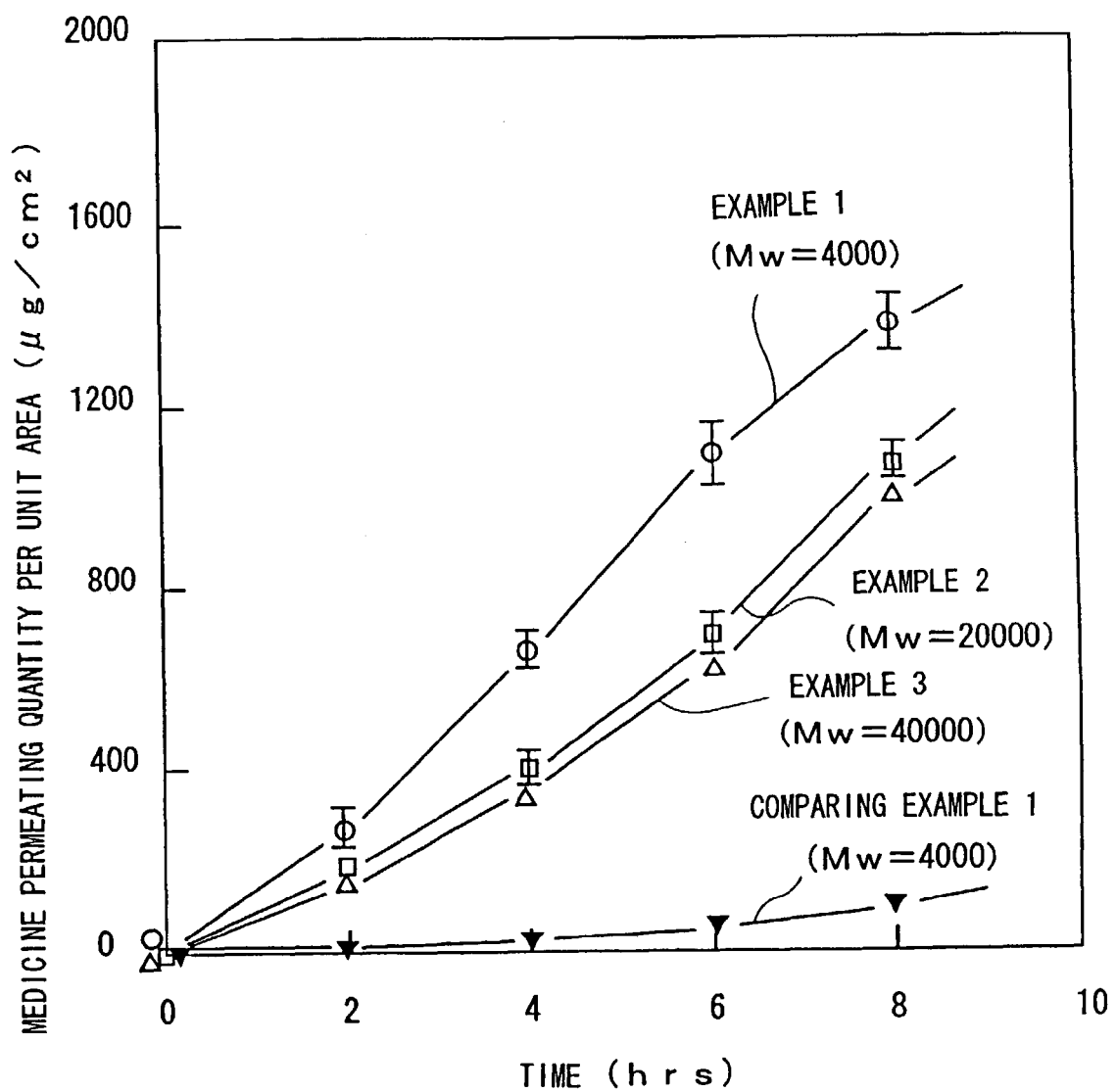
FIG. 14 is a view for explaining the relationship between a medicine delivery quantity and time when the elastic member is used in the first embodiment.
Figure 15:
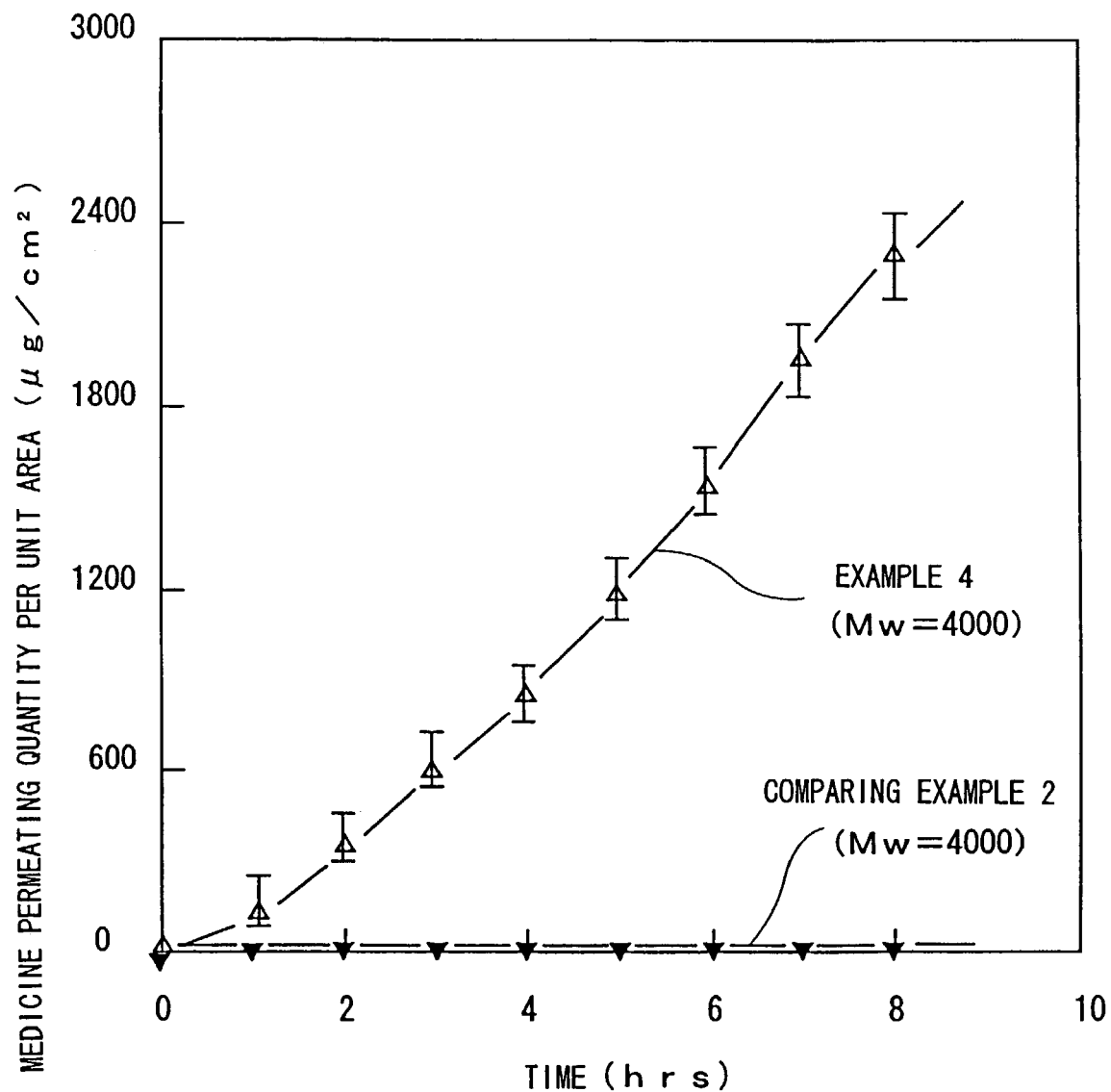
FIG. 15 is a view for explaining the relationship between a medicine delivery quantity and time when the bubbles are used in the first embodiment.

The obtained respective results are shown in FIG. 14, FIG. 15 and Table 1. As can be understood from these results, it is confirmed that, possibly due to the fact that the pressure is not applied to the medicine in the comparing example 1, compared to the example 1, the permeating quantity is decreased to several %. It is also confirmed that the medicine is not permeated at all in the comparing example 2.

TABLE 1

| | Molecular weight of medicine | Pressure applying (method) | Mechanical stimulus | Permeating quantity (μg/cm$^2$) 2 Hrs | Permeating quantity (μg/cm$^2$) 8 Hrs |
|---|---|---|---|---|---|
| example 1 | 4,000 | Adopted (resilient member) | adopted | 270 | 1390 |
| example 2 | 20,000 | Adopted (resilient member) | adopted | 190 | 1090 |
| example 3 | 40,000 | Adopted (resilient member) | adopted | 145 | 980 |
| example 4 | 4,000 | Adopted (bubbles) | adopted | 360 | 2300 |
| comparing example 1 | 4,000 | not adopted | adopted | 8 | 95 |
| comparing example 2 | 4,000 | not adopted | not adopted | 0 | 0 |

Example 6

1. Preparation of Percutaneous Absorption System

In the example 6, an liquid leaking preventing layer is formed such that a stainless steel pin having a length of 1.55 mm and a diameter of 0.26 mm is inserted into and fixed to the liquid leaking preventing layer of the example 1 thus providing a projection to the liquid leaking preventing layer. Subsequently, the liquid leaking preventing layer having the projection is laminated to the polyethylene foamed body of the medicine reservoir portion by way of the second adhesive layer such that a distal end portion of the stainless steel pin is positioned perpendicular to the first substrate having medicine non-permeating property. Except for the above-mentioned constitution, the percutaneous absorption system of the example 6 is prepared in the same manner as that of the example 1.

2. Evaluation In Vitro of Percutaneous Absorption System

In the same manner as the example 1, a skin which is cut out from a hairless rat is mounted on the vertical diffusion cell and the percutaneous absorption system shown in FIG. 9 from which the peel-off film is removed is adhered to a stratum corneum side of the skin of the hairless rat.

Then, in a state that purified water of a temperature of 32° C. is inserted into a receptor of the vertical diffusion cell, the stainless steel pin mounted on the medicine reservoir portion is pushed so as to allow the stainless steel pin to pierce and penetrate the skin of the hairless rat by way of the substrate having medicine non-permeating substrate.

Then, after returning the stainless steel pin to the original position, a cumulative quantity (permeating quantity per unit area) of the FITC dextran, which is permeated to the purified water in the receptor from the percutaneous absorption system through the skin of the hairless rat, is measured.

Here, the quantitative analysis of the FITC dextran concentration in the purified water is performed using a fluorometric luminous intensity meter RF-5300PC (manufactured by Shimadzu Corporation). An obtained result is shown in Table 2 and FIG. 16.

From this result, it is confirmed that, also in this example 6, the measured permeating quantity of FITC dextran and time are changed about in a straight line and the FITC dextran having a weight-average molecular weight of 4000 is delivered at a fixed rate.

Example 7 and Example 8

Except for that the liquid leaking preventing layer provided with the projection used in the example 6 is also used in the example 7 and the example 8, the percutaneous absorption system is prepared in the same manner as the example 2 and the example 3.

Then, in the same manner as the example 6, using the vertical diffusion cell, a cumulative quantity (permeating quantity per unit area) of FITC dextran, which is permeated through the skin of the hairless rat, is measured. Obtained results are respectively shown in Table 2 and FIG. 16.

Example 9

1. Preparation of Percutaneous Absorption System

Except for that the liquid leaking preventing layer used in the example 6 is also used in the example 9, the percutaneous absorption system is prepared in the same manner as the example 4.

Then, in the same manner as the example 6, using the vertical diffusion cell, a cumulative quantity (permeating quantity per unit) of FITC dextran, which is permeated through the skin of the hairless rat, is measured. Obtained results are respectively shown in Table 2 and FIG. 18.

Example 10

1. Preparation of Percutaneous Absorption System

Except for that the liquid leaking preventing layer used in the example 6 is also used in the example 10, the percutaneous absorption system is prepared in the same manner as the example 5.

2. Evaluation of Percutaneous Absorption System In Vivo Skin Permeating Experiment In the same manner as the example 5, the percutaneous absorption system from which the peel-off film is removed is adhered to an abdomen of the hairless rat which is under urethane anesthetization and a stainless steel pin mounted on the medicine reservoir portion is pushed thus allowing the stainless steel pin to pierce and penetrate a skin of a hairless rat by way of the substrate having medicine non-permeating property. Then, after returning the stainless steel pin to the original position, the concentration of insulin in the blood plasma of the hairless rat is time-sequentially measured by a method similar to the method adopted by the example 5. The concentration of insulin in the blood plasma of the hairless rat is 15 µU/mL after 1 hour, 9.15 µU/mL after 3 hours, and 8.1 µU/mL after 5 hours. From these results, it is confirmed that the insulin, which is an aqueous high-molecular medicine, can also be administered by permeating the insulin through the skin.

Example 11

Figure 17:
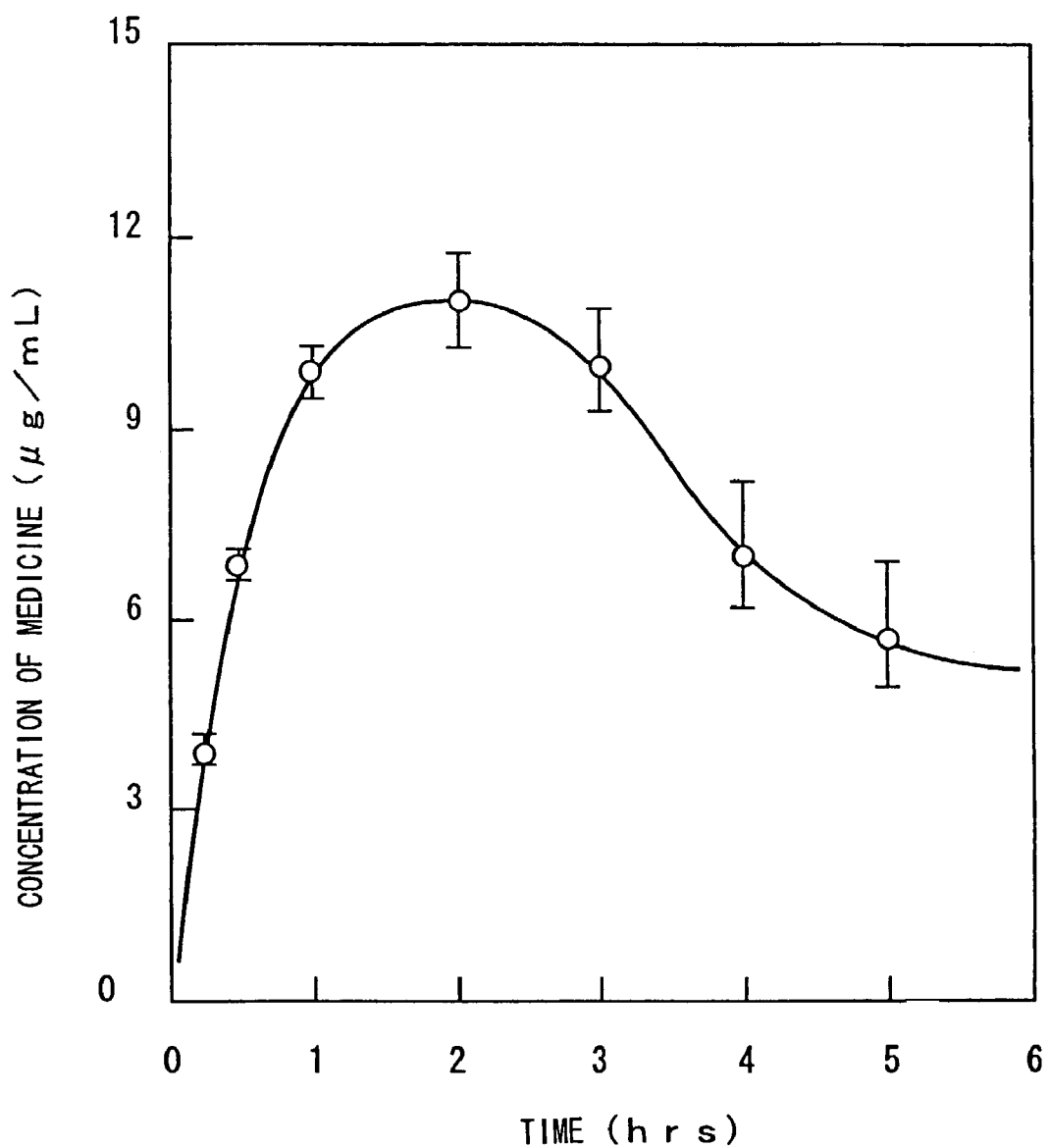
FIG. 17 is a view for explaining the relationship between the concentration of medicine in blood plasma and time when the elastic member is used in the second embodiment.

After removing the peel-off film of the percutaneous absorption system used in the embodiment 6, the percutaneous absorption system is adhered to an abdomen of the hairless rat, which is under urethane anesthetization. Then, a stainless steel pin is pushed thus allowing the stainless steel pin to pierce and penetrate a skin of a hairless rat by way of the substrate having medicine non-permeating property. Thereafter, the stainless steel pin is returned to the original position and an experiment to administer the FITC dextran into the body of the hairless rat is performed. After starting the administration of the medicine, blood is sampled from a vein time-sequentially. The sampled blood is subjected to the centrifugal separation at a rotational speed of 15,000 rpm for five minutes at a temperature of 4° C. The obtained supernatant liquid (blood plasma) is diluted twice using a physiological salt solution and, thereafter, the FITC dextran concentration is measured using a fluorometric luminous intensity meter RF-5300PC. An obtained result is shown FIG. 17. The measured FITC dextran concentration is gradually elevated after starting the administration and reaches a peak after two hours elapses. Thereafter, the FITC dextran concentration is gradually lowered. Further, it is confirmed that the FITC dextran remains in the body even after five hours elapses from the starting of the administration. From these results, it is confirmed that the FITC dextran having a weight-molecular weight of 4,000 can also administered to the hairless rat continuously.

Comparing Examples 3 and 4

In a comparing example 3, a percutaneous absorption system is prepared and evaluated in the same manner as the example 1 except for that in place of the medicine reservoir portion formed of the polyethylene foamed body in the example 6, a medicine reservoir portion which is wholly formed of a PET film is prepared and the medicine is filled in the medicine reservoir portion such that the medicine assumes 90% with respect to the inner volume (100%) of the liquid reservoir portion thus preventing the generation of the inner pressure in the medicine.

Further, in a comparing example 4, a percutaneous absorption system is prepared and evaluated in the same manner as the comparing example 3 except for that breaking of the substrate by the projection in the comparing example 3 is not performed in the comparing example 4.

Figure 16:
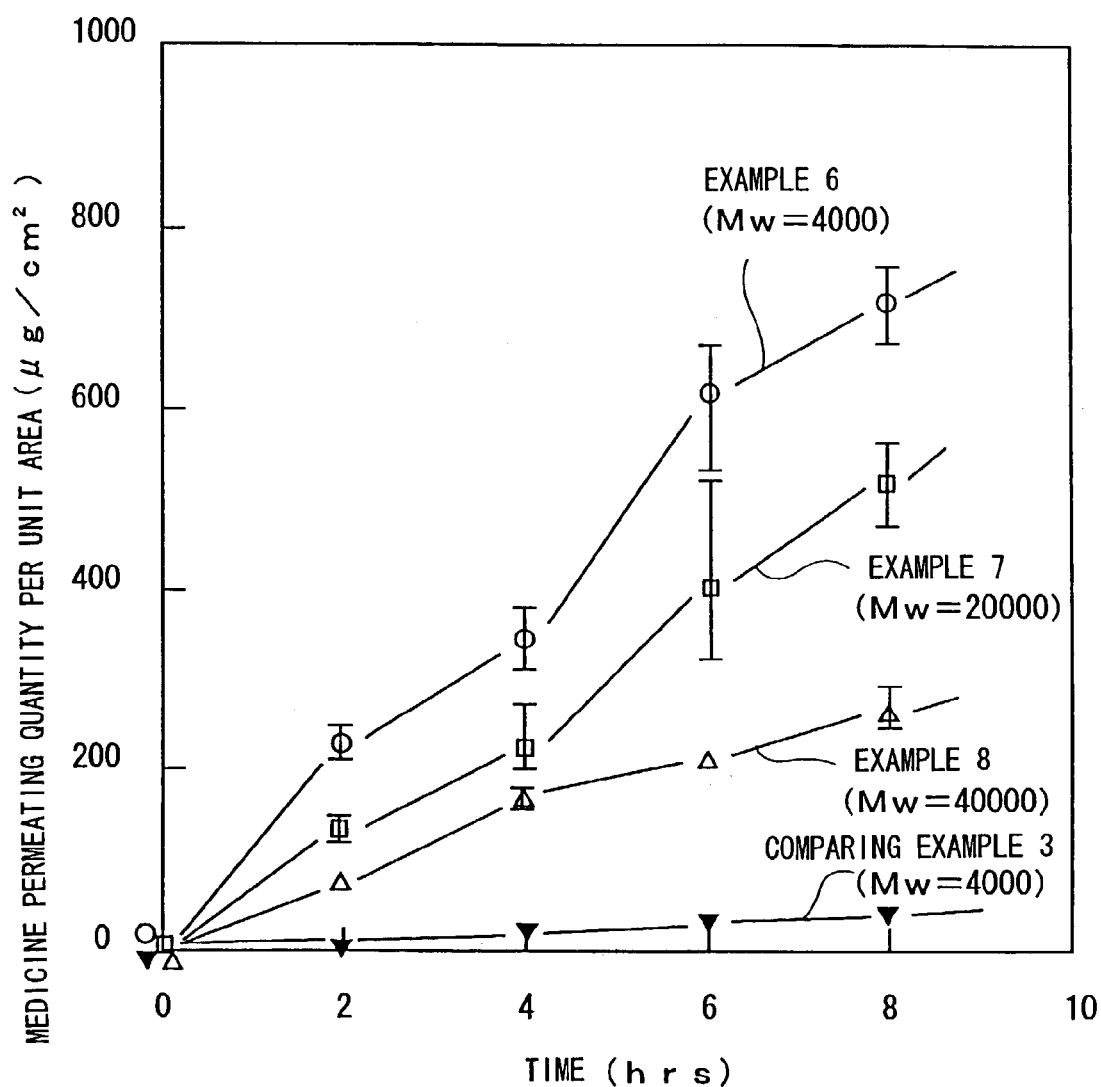
FIG. 16 is a view for explaining the relationship between a medicine delivery quantity and time when the elastic member is used in the second embodiment.
Figure 18:
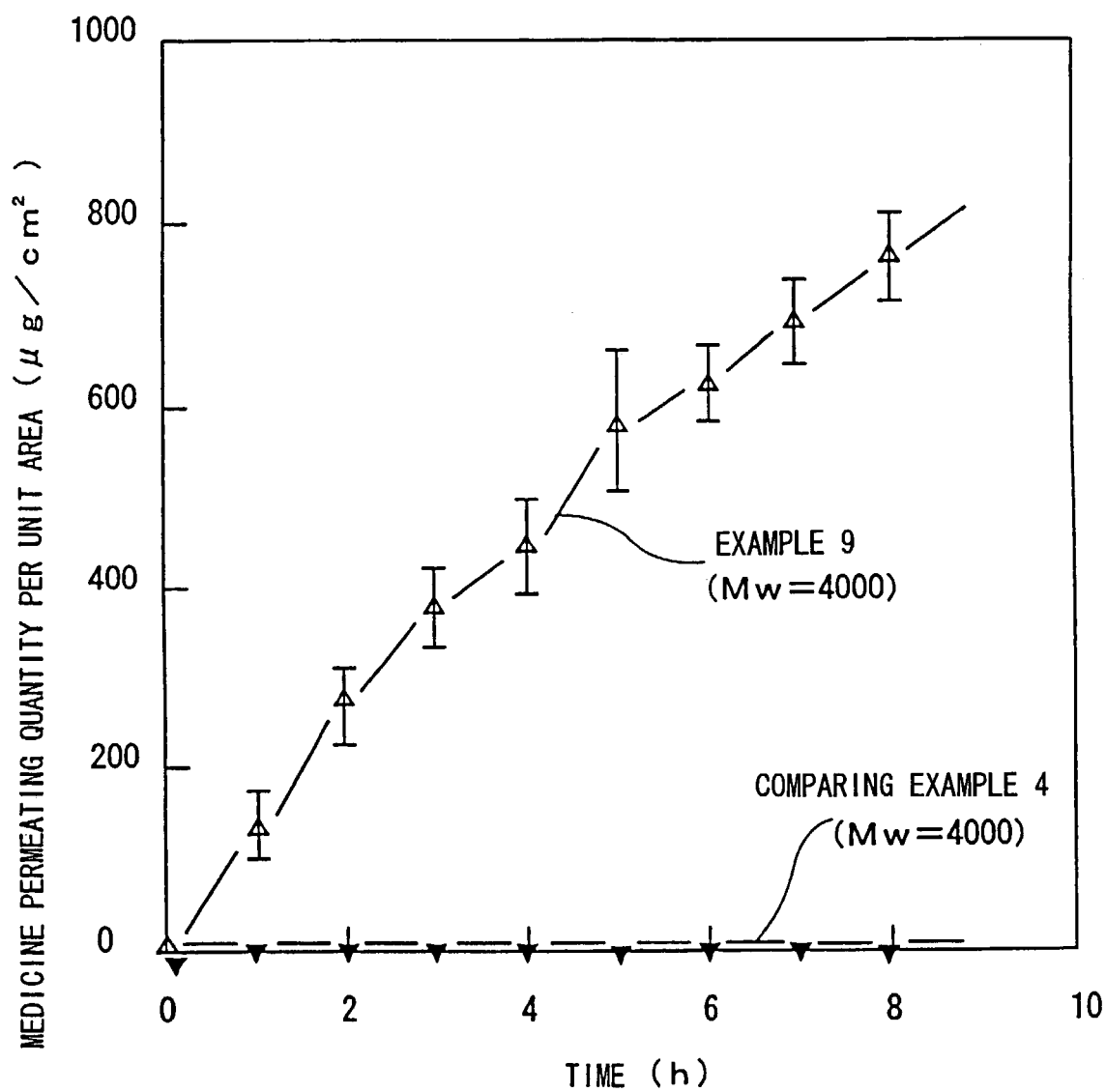
FIG. 18 is a view for explaining the relationship between a delivery quantity of medicine and time when the bubbles are used in the second embodiment.
Figure 19:
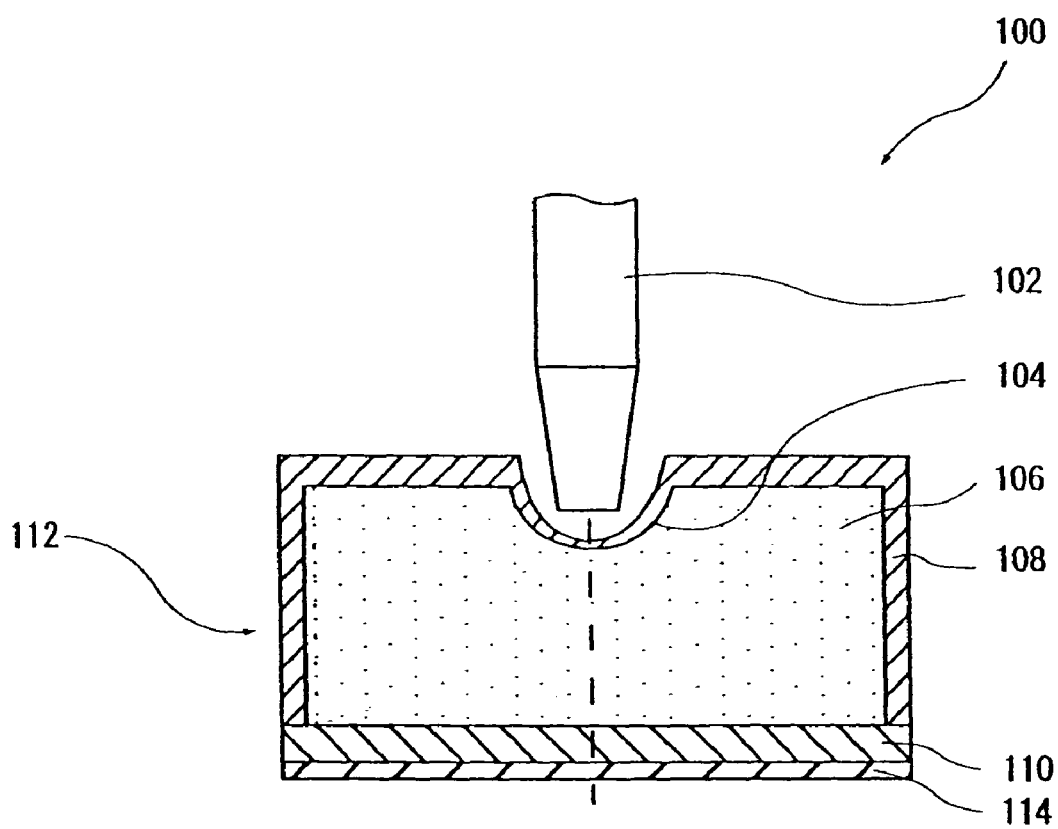
FIG. 19 is a view for explaining the structure of a conventional percutaneous absorption system using a jet injector.
Figure 20:
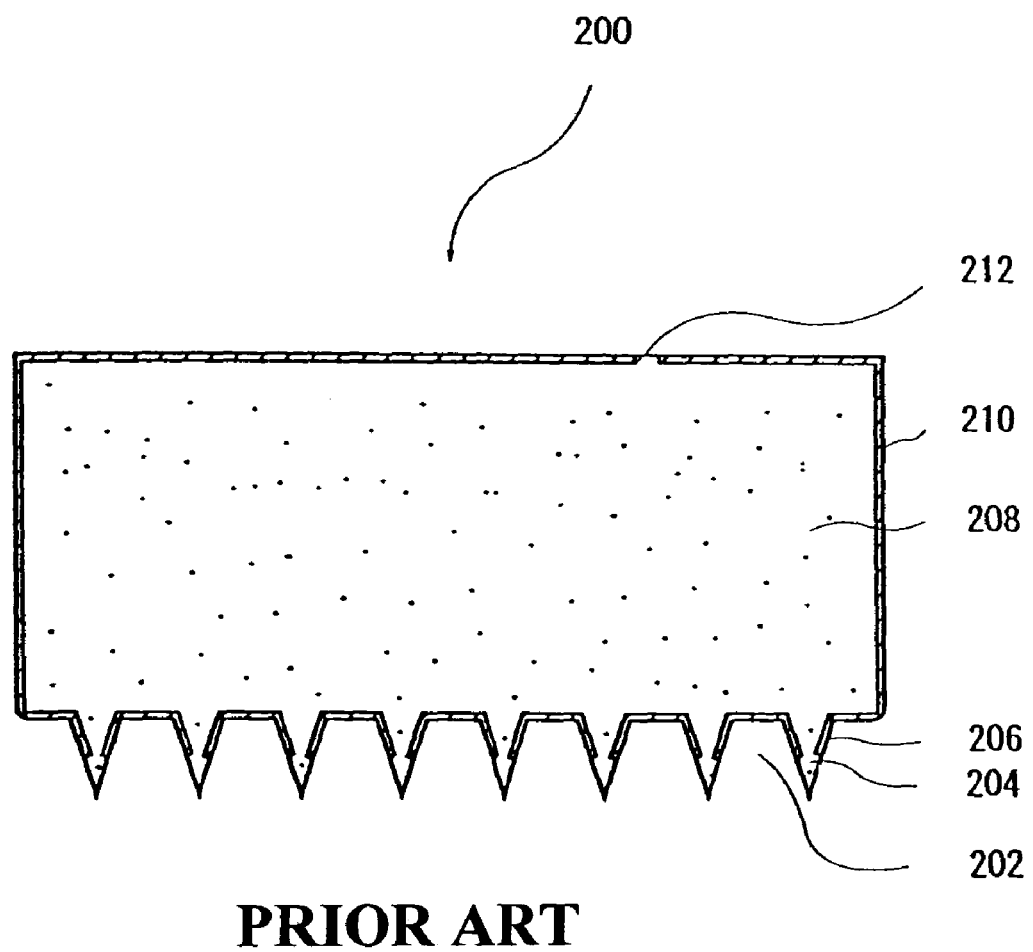
FIG. 20 is a view for explaining the structure of a conventional percutaneous absorption system having micro-pins.

The obtained respective results are shown in FIG. 16 and FIG. 18. As can be understood from these results, it is confirmed that, possibly due to the fact that the pressure is not applied to the medicine in the comparing example 3, compared to the example 6, the permeating quantity is decreased to several %. It is also confirmed that the medicine is not permeated at all in the comparing example 4.

TABLE 2

| | Molecular weight of medicine | Pressure applying (method) | Projection | Permeating quantity(µg/cm$^2$) | |
| --- | --- | --- | --- | --- | --- |
| | | | | 2 Hrs | 8 Hrs |
| example 6 | 4,000 | Adopted (resilient member) | adopted | 228 | 724 |
| example 7 | 20,000 | Adopted (resilient member) | adopted | 133 | 520 |
| example 8 | 40,000 | Adopted (resilient member) | adopted | 70 | 270 |
| example 9 | 4,000 | Adopted (bubbles) | adopted | 278 | 762 |
| Comparing example 3 | 4,000 | not adopted | adopted | 5 | 43 |
| Comparing example 4 | 4,000 | not adopted | not adopted | 0 | 0 |

As has been described heretofore, according to the percutaneous absorption system and the percutaneous absorption method of the present invention, by applying pressure to the medicine held in the medicine reservoir portion and by breaking the substrate by the mechanical stimulus, it is possible to provide the percutaneous absorption system which exhibits the excellent portability and adhesiveness and can make the medicine formed of an oligomer or the high molecular weight which is generally not suitable for percutaneous absorption easily and continuously percutaneously absorbed.

Further, according to the percutaneous absorption system and the percutaneous absorption method of the present invention, by using such system and method in combination with the administration of medicine by a usual injector, it is possible to achieve the more effective administration of medicine. That is, by administering the medicine using the injector, it is possible to obtain the immediate effectivity of the medicine and with the provision of this percutaneous absorption system, it is possible to continuously administer the medicine so that the concentration of the medicine in the blood can be held at a fixed value.

What is claimed is:

1. A percutaneous absorption system comprising a medicine reservoir portion having a medicine holding portion which holds medicine which is insulin, calcitonin or vasopressin therein and a support portion for supporting the medicine reservoir portion on the skin surface, the support portion including an adhesive layer and a substrate having medicine non-permeating property which thickness is of 5 to 1000 μM,
   wherein a portion or the whole of the medicine reservoir portion comprises an elastic member,
   the medicine is held in the medicine holding portion under pressure in an initial value of about $1.1 \times 10^5$ Pa or more,
   a projection is provided inside of the medicine reservoir portion,
   and the substrate having medicine non-permeating property in the support portion is breakable upon receiving a mechanical stimulus given by the projection.

2. The percutaneous absorption system according to claim 1, wherein the elastic member is a foamed body.

3. The percutaneous absorption system according to claim 1, wherein the medicine reservoir portion has a substantially cylindrical shape and defines the medicine holding portion inside thereof.

4. The percutaneous absorption system according to claim 1, wherein the projection has a distal end portion thereof extended downwardly and arranged substantially in a direction perpendicular to the substrate having medicine non-permeating property.

5. The percutaneous absorption system according to claim 1, wherein the projection is mounted on an upper surface of the medicine reservoir portion and the upper surface of the medicine reservoir portion is formed of the elastic member.

6. The percutaneous absorption system according to claim 1, wherein a pushing portion which is served for pushing down the projection is formed on an end portion of the projection.

7. A percutaneous absorption system comprising a medicine reservoir portion having a medicine holding portion which holds medicine which is insulin, calcitonin or vasopressin therein and a support portion for supporting the medicine reservoir portion on the skin surface, the support portion including an adhesive layer and a substrate having medicine non-permeating property which thickness is of 5 to 1000 μm,
   wherein gas which applies pressure to the medicine held in the medicine reservoir portion in an initial value of about $1.1 \times 10^5$ Pa or more, is introduced inside of the medicine holding portion,
   a projection is provided inside of the medicine reservoir portion,
   and the substrate having medicine non-permeating property in the support portion is breakable upon receiving a mechanical stimulus given by the projection.

8. The percutaneous absorption system according to claim 7, wherein a portion or the whole of the medicine reservoir portion is constituted of an elastic member for applying pressure to the medicine held in the medicine holding portion.

9. A percutaneous absorption method which uses a percutaneous absorption system comprising a medicine reservoir portion having a medicine holding portion which holds medicine which is insulin, calcitonin or vasopressin therein and a support portion for supporting the medicine reservoir portion to the skin surface, the support portion including an adhesive layer and a substrate having medicine non-permeating property which thickness is of 5 to 1000 μm, a portion or the whole of the medicine reservoir portion comprises an elastic member, and the medicine is held in the medicine holding portion under pressure in an initial value of about $1.1 \times 10^5$ Pa or more
   wherein the method comprises mounting the percutaneous absorption system to the skin surface,
   breaking at least the substrate having medicine non-permeating property in the support portion using a mechanical stimulus given by a projection provided inside of the medicine reservoir portion so that delivery of the medicine begins by pressure applied to the medicine in the initial value of about $1.1 \times 10^5$ Pa or more.

10. A percutaneous absorption method which uses a percutaneous absorption system comprising a medicine reservoir portion having a medicine holding portion which holds medicine which is insulin, calcitonin or vasopressin therein and a support portion for supporting the medicine reservoir portion on the skin surface, the support portion including an adhesive layer and a substrate having medicine non-permeating property which thickness is of 5 to 1000 μm,
   wherein the method comprises mounting the percutaneous absorption system to the skin surface,
   breaking at least the substrate having medicine non-permeating property in the support portion using a mechanical stimulus given by a projection provided inside of the medicine reservoir portion,
   and delivering the medicine by applying pressure to the medicine in an initial value of about $1.1 \times 10^5$ Pa or more, using gas previously introduced into the medicine reservoir portion.

11. The percutaneous absorption system according to claim 1, wherein the initial value is up to about $2.0 \times 10^5$ Pa.

12. The percutaneous absorption system according to claim 1, wherein the initial value is up to about $1.8 \times 10^5$ Pa.

13. The percutaneous absorption system according to claim 1, wherein the medicine comprises insulin.

14. The percutaneous absorption system according to claim 7, wherein the medicine comprises insulin.

15. The percutaneous absorption method according to claim 9, wherein the medicine comprises insulin.

16. The percutaneous absorption method according to claim 9, wherein the medicine is administered into a stratum corneum of skin using the projection which penetrates the skin.

17. The percutaneous absorption method according to claim 10, wherein the medicine comprises insulin.

18. The percutaneous absorption method according to claim 10, wherein the medicine is administered into a stratum corneum of skin using the projection which penetrates the skin.

* * * * *

UNITED STATES PATENT AND TRADEMARK OFFICE
CERTIFICATE OF CORRECTION

PATENT NO. : 7,858,112 B2
APPLICATION NO. : 10/372957
DATED : December 28, 2010
INVENTOR(S) : T. Hatanaka et al.

It is certified that error appears in the above-identified patent and that said Letters Patent is hereby corrected as shown below:

On cover page, Item [73] Assignees should be
"LINTEC CORPORATION, Tokyo (JP); Kenji SUGIBAYASHI, Saitama (JP)"
instead of "LINTEC CORPORATION, Tokyo (JP); Kenji SUGIBIAYASHI Saitama (JP)".

Signed and Sealed this
Nineteenth Day of July, 2011

David J. Kappos
*Director of the United States Patent and Trademark Office*